United States Patent [19]

Bergey et al.

[11] Patent Number: 5,669,394
[45] Date of Patent: Sep. 23, 1997

[54] BIOSAMPLE ASPIRATOR

[75] Inventors: Karl H. Bergey, Norman; William H. Diepenbrock, Bethany, both of Okla.

[73] Assignee: The Board Of Regents of the Univ. of Oklahoma, Norman, Okla.

[21] Appl. No.: 362,698

[22] Filed: Dec. 22, 1994

Related U.S. Application Data

[60] Continuation-in-part of Ser. No. 779,699, Oct. 21, 1991, Pat. No. 5,387,191, which is a division of Ser. No. 602,580, Oct. 24, 1990, Pat. No. 5,081,999, which is a continuation of Ser. No. 307,403, Feb. 6, 1989, Pat. No. 4,982,739.

[51] Int. Cl.[6] ............................................. A61B 10/00
[52] U.S. Cl. ........................... 128/750; 128/753; 604/37; 604/153
[58] Field of Search ................................. 128/749–755, 128/760, 763–766; 604/22, 27, 28, 35, 43, 44, 131, 151, 153

[56] References Cited

U.S. PATENT DOCUMENTS 3,477,423  11/1969  Griffith et al.
3,819,091  6/1974  Hollender et al. ........................... 222/327
4,493,694  1/1985  Wuchinich ................................... 604/22

OTHER PUBLICATIONS

W. J. Catalona & W. W. Scott, Carcinoma of the Prostrate, Campbell's Urology, 5th ed., vol. 2, pp. 1477–1480 (W. B. Saunders Co., 1986).
The Clinical Cancer Letter, vol. 10, No. 8, Reston, Virginia, Aug. 1987.
Oncology Viewpoints, vol. 2, No. 5, LP Communications, Inc., New York, N.Y., 1988, pp. 4–17.

Primary Examiner—Max Hindenburg
Attorney, Agent, or Firm—Dunlap & Codding, P.C.

[57] ABSTRACT

A fine-needle aspirator for collecting a biosample from a subject into a closed sterile system. The aspirator is adapted for use with a variety of needles and comprises a motor drive pump capable of continuous suction in a biosample collection system. The biosample collection system may comprise a biosample connector such as elastomeric tubing in communication with the needle and a collection space in a biosample container whereby a biosample collected by the needle may be transferred to the collection space. A flushing substance flushes the biosample through the biosample collection system. Additives may be added to the biosample after collection in order to treat, preserve or analyze the biosample.

60 Claims, 13 Drawing Sheets

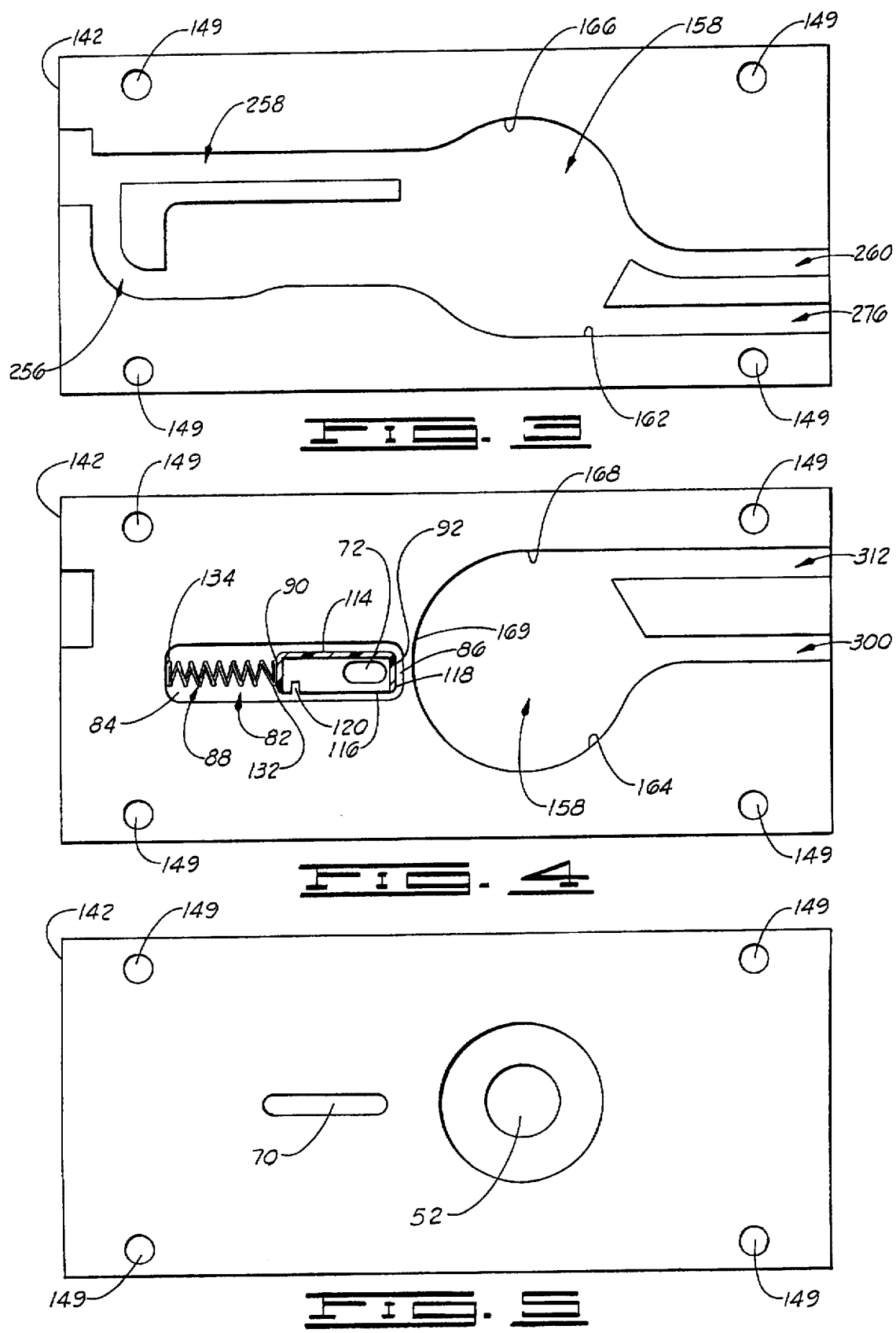

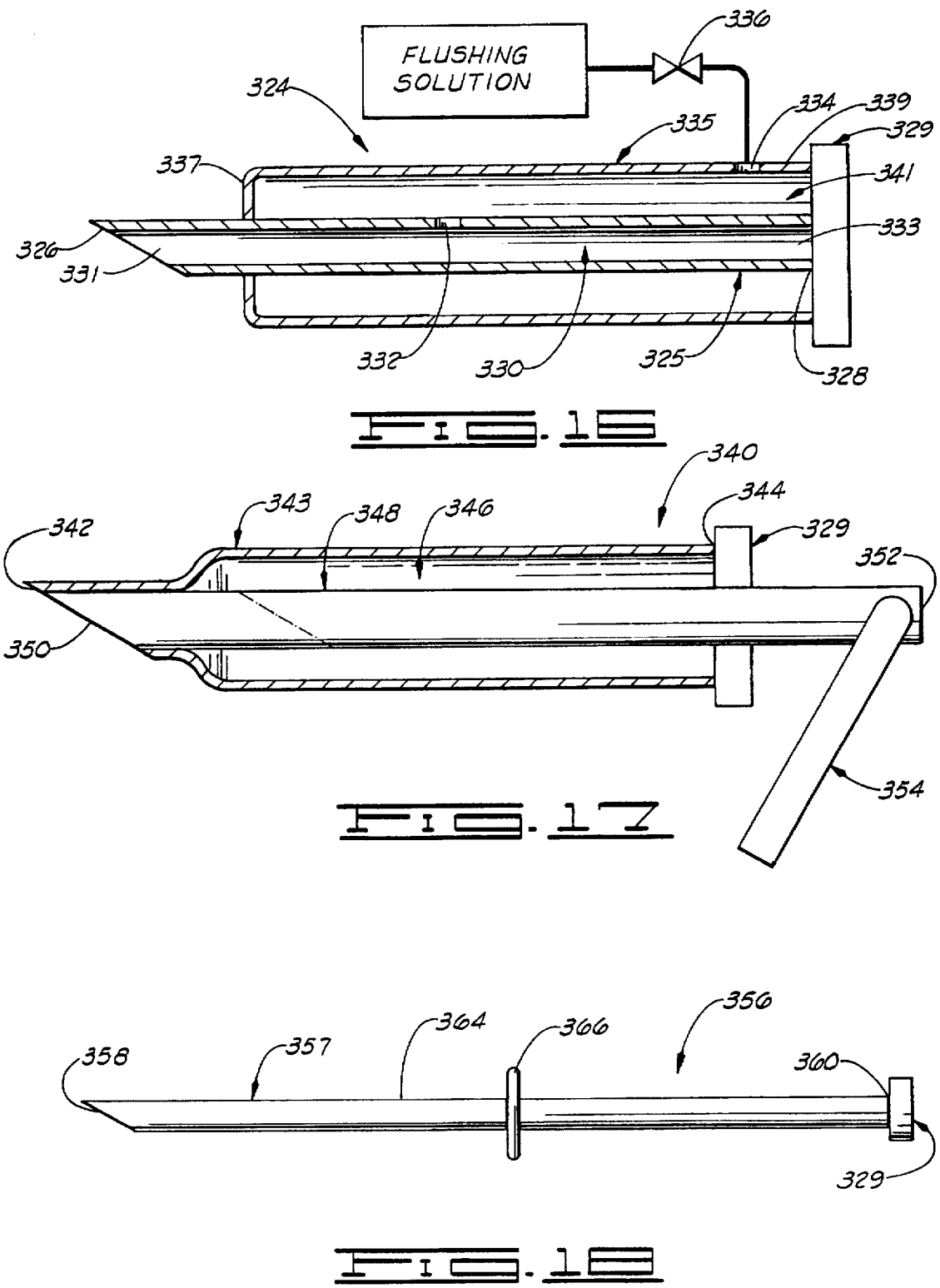

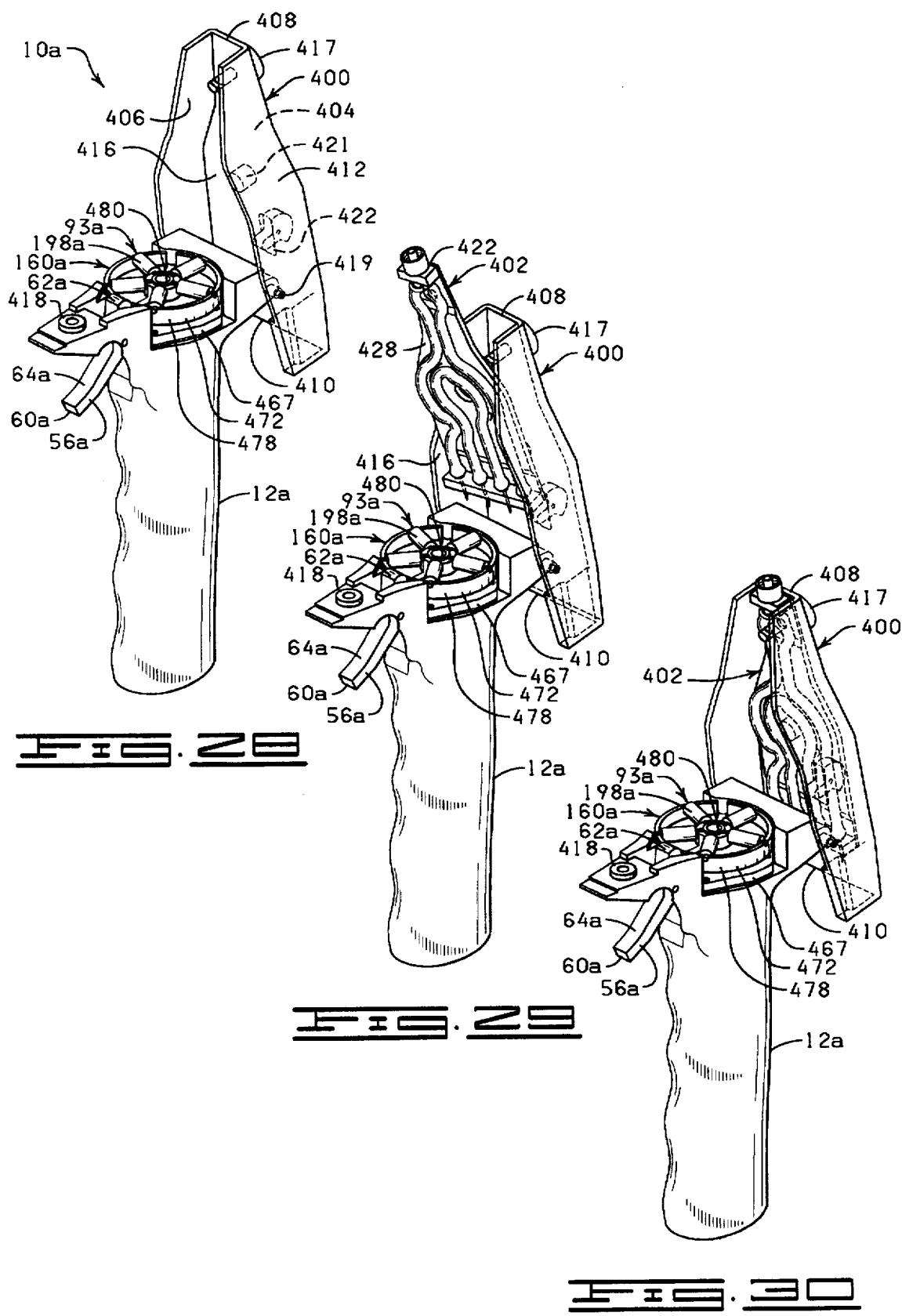

5,669,394

1

BIOSAMPLE ASPIRATOR

CROSS-REFERENCE TO RELATED APPLICATIONS

This application is a continuation-in-part of U.S. Ser. No. 07/779,699, filed Oct. 21, 1991, entitled BIOSAMPLE ASPIRATOR U.S. Pat. No. 5,387,191; which is a divisional of U.S. Ser. No. 07/602,580, filed Oct. 24, 1990, entitled BIOSAMPLE ASPIRATOR, now U.S. Pat. No. 5,081,999, issued on Jan. 21, 1992; which is a continuation of U.S. Ser. No. 07/307,403, filed Feb. 6, 1989, entitled BIOSAMPLE ASPIRATOR, now U.S. Pat. No. 4,982,739, issued on Jan. 8, 1991.

FIELD OF THE INVENTION

The present invention relates generally, but not by way of limitation, to methods and devices for obtaining biological samples from a subject.

BRIEF DESCRIPTION OF THE DRAWINGS

FIGS. 2–5 are horizontal cross sections of the pump housing of the present invention. FIG. 5 is the lowest section upon which respectively sections in FIGS. 4, 3 and 2 are mounted.

FIG. 2 is a top plan view of a cross section of the pump housing of the present invention.

FIG. 3 is a top plan view of a cross section of the pump housing of the present invention showing a portion of the pump housing component space.

FIG. 4 is a top plan view of a cross section of the pump housing of the present invention showing a portion of the pump housing component space including a portion of the trigger aperture which contains a slide spring attached to the trigger slide shown in a horizontal cross section and the rod support member space.

FIG. 5 is a top plan view of the lowest cross section of the pump housing of the present invention showing a portion of the trigger aperture and the pump housing shaft aperture.

FIG. 16 is a side elevational view of the flushing needle.

FIG. 17 is a side elevational view of the obturator needle.

2

FIG. 18 is a side elevational view of the flanged needle.

Figure 19:
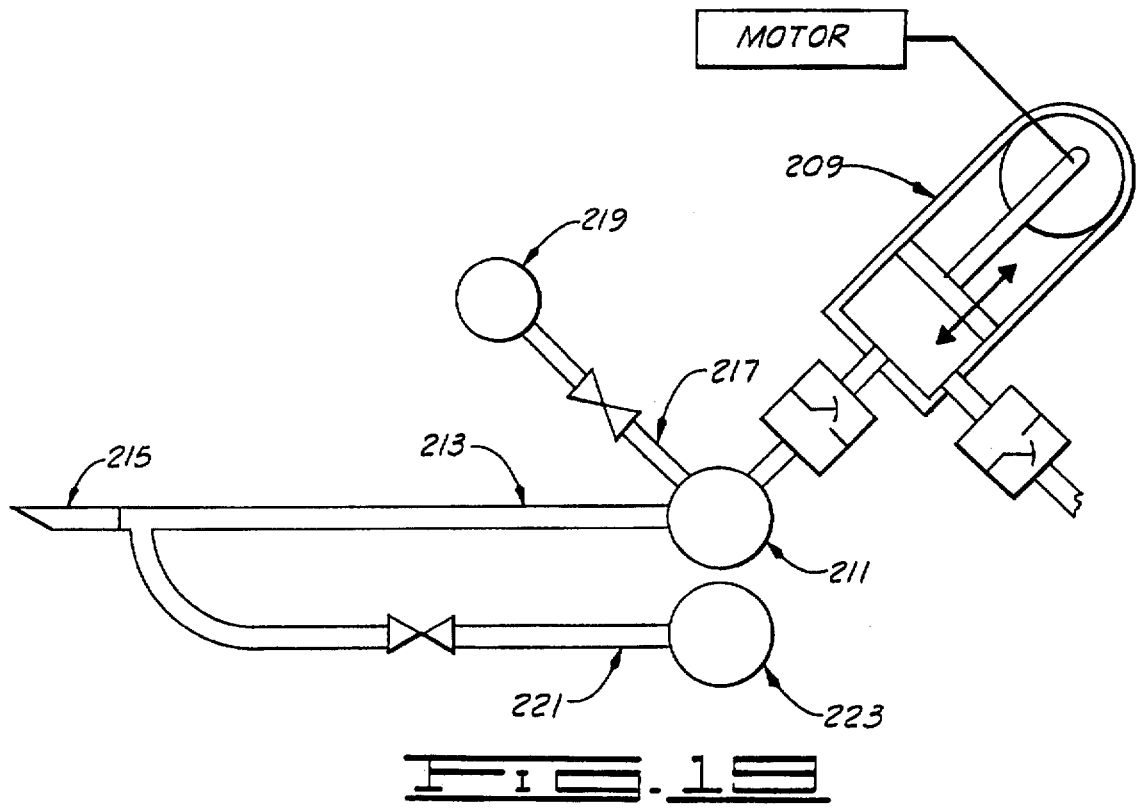

FIG. 19 is a schematic drawing of the aspirator in accordance with the present invention using a piston pump.

Figure 20:
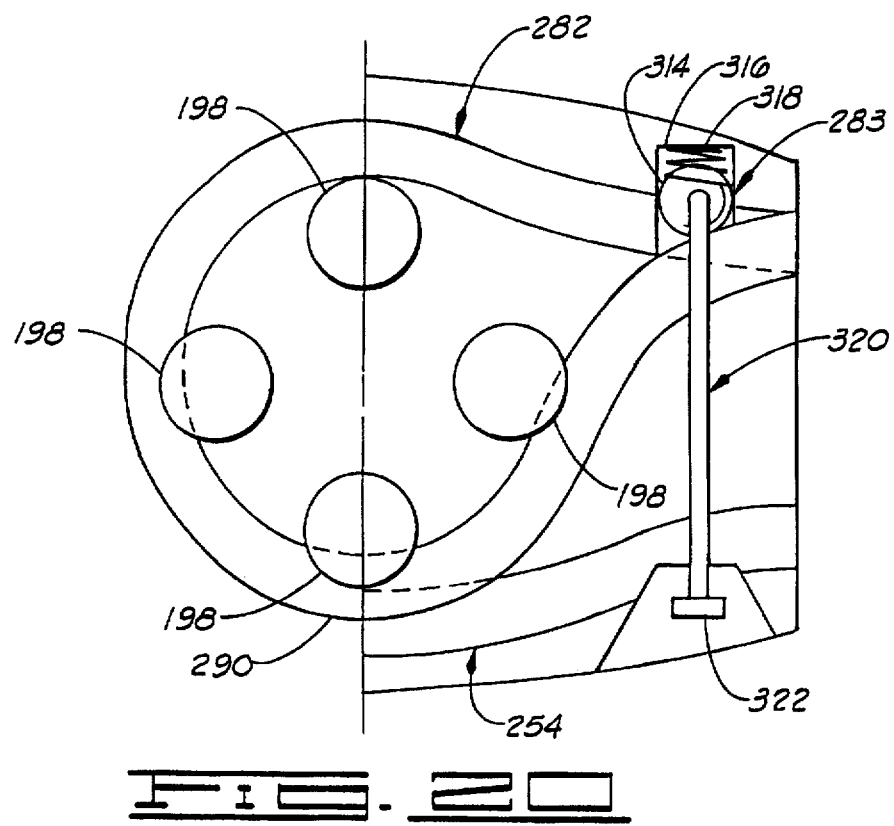

FIG. 20 is a top plan view of a horizontal cross section of the peristaltic pump with the additive connector and the additive regulator.

Figure 21:
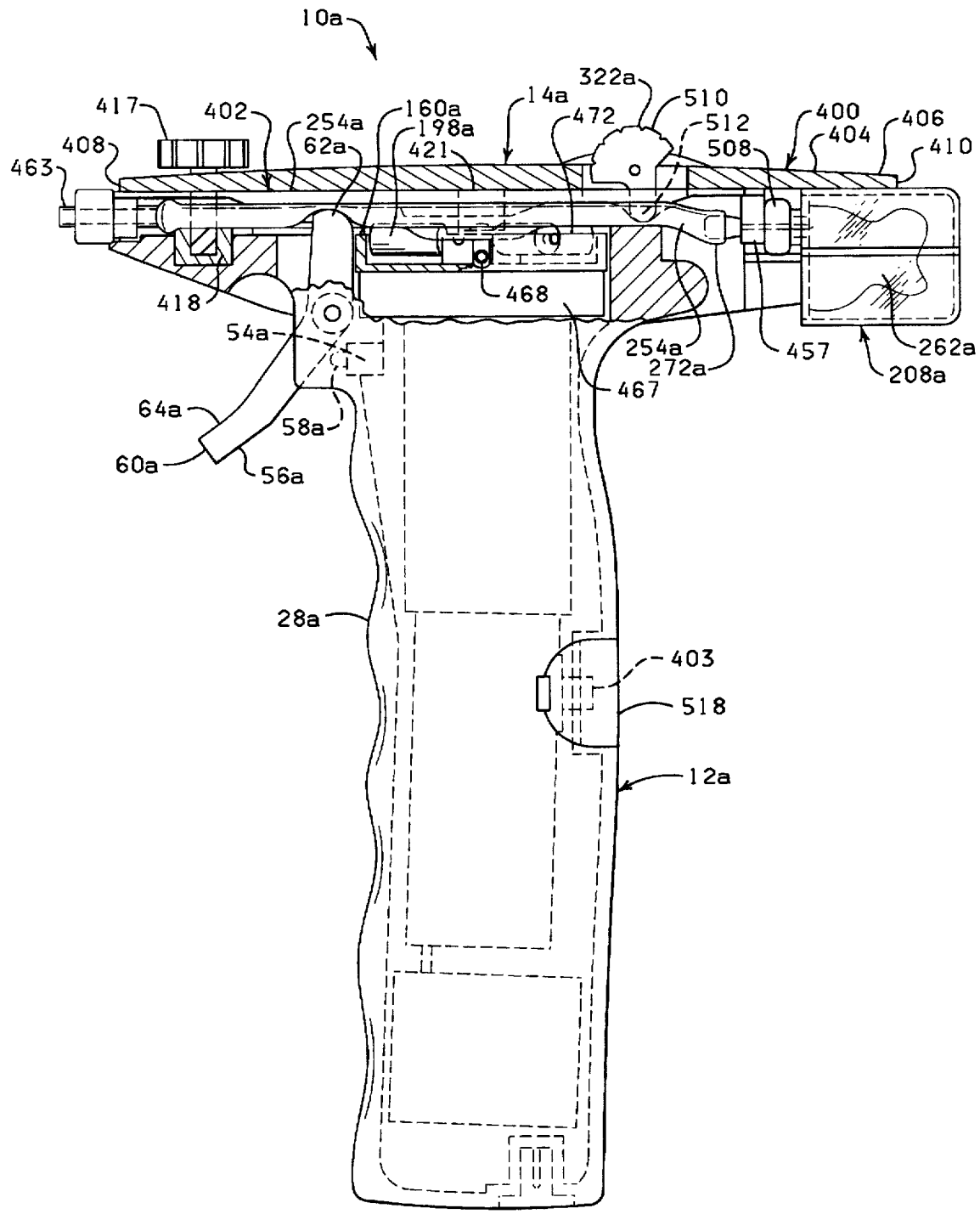

FIG. 21 is a side elevational view of a modified biosample aspirator.

Figure 22:
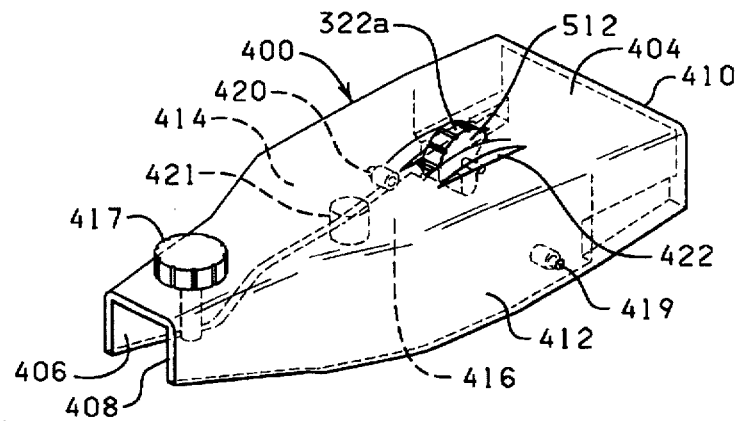

FIG. 22 is a perspective view of the hinged lid of the modified biosample aspirator of FIG. 21.

Figure 23:
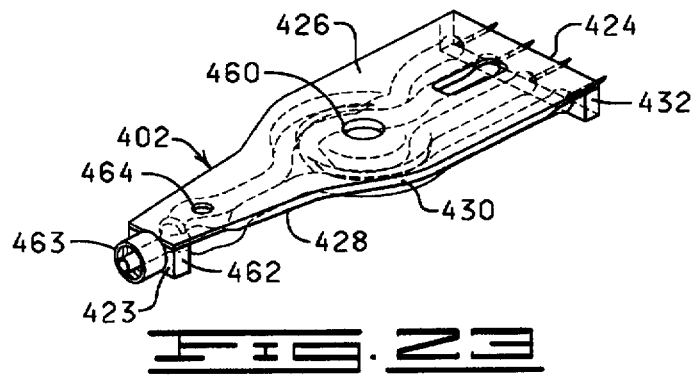

FIG. 23 is a perspective view of the card of the modified biosample aspirator of FIG. 21, showing the biosample connector, the flushing connector and the additive connector.

Figure 24:
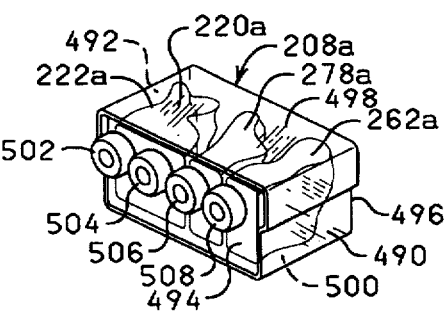

FIG. 24 is a perspective view of the modified container compartment of the modified biosample aspirator of FIG. 21.

Figure 25:
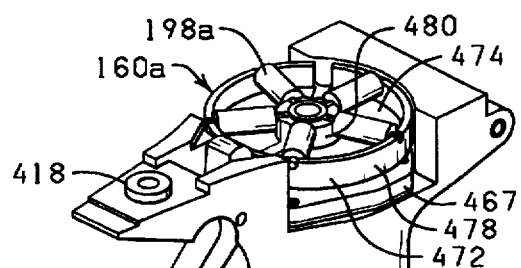

FIG. 25 is a perspective view of the pump housing component space showing the modified rod support member and plurality of rods of the modified biosample aspirator of FIG. 21.

Figure 26:
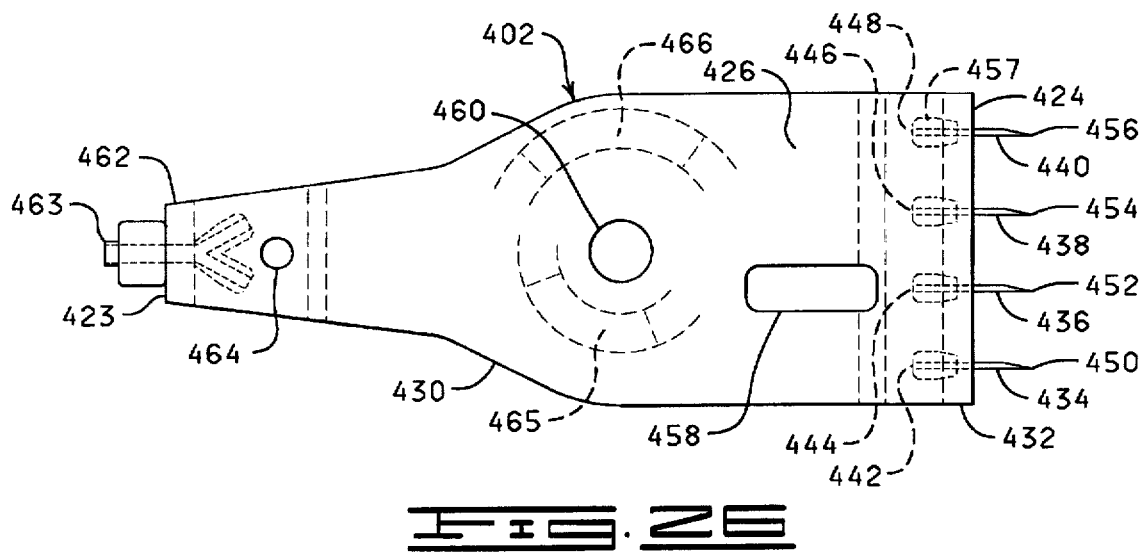

FIG. 26 is a top plan view of the card of the modified biosample aspirator of FIG. 21.

Figure 27:
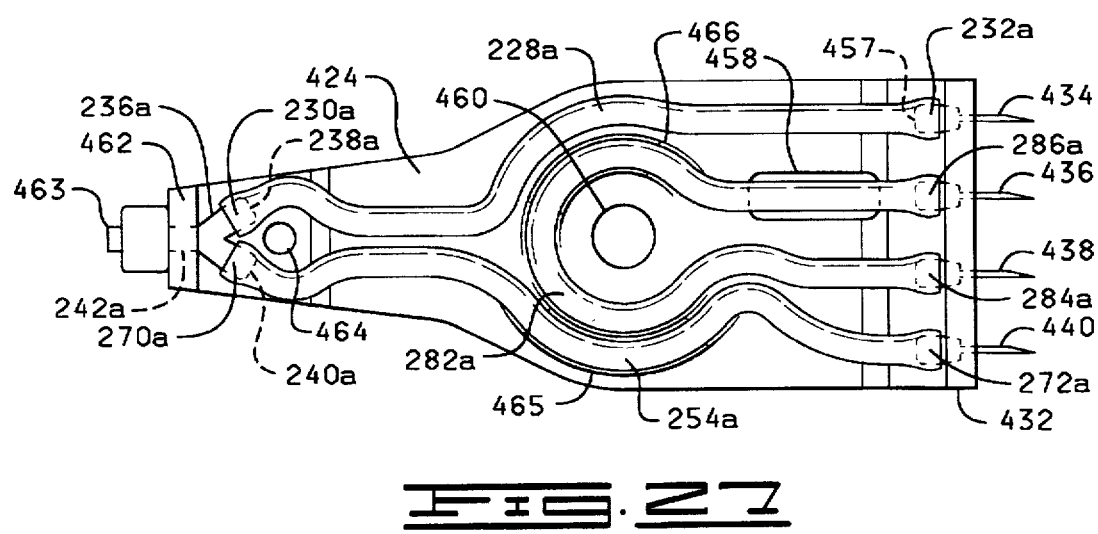

FIG. 27 is a bottom plan view of the card of the modified biosample aspirator of FIG. 21.

FIG. 28 is a perspective view of the modified biosample aspirator of FIG. 21, showing the hinged lid tilted upward in a position to receive a card, and showing both the pump housing component space and the card space.

FIG. 29 is a perspective view of the modified biosample aspirator of FIGS. 21 and 28, but showing a card being inserted in the card space.

FIG. 30 is a perspective view of the modified biosample aspirator of FIGS. 21 and 28, but showing a card inserted in the card space.

Figure 31:
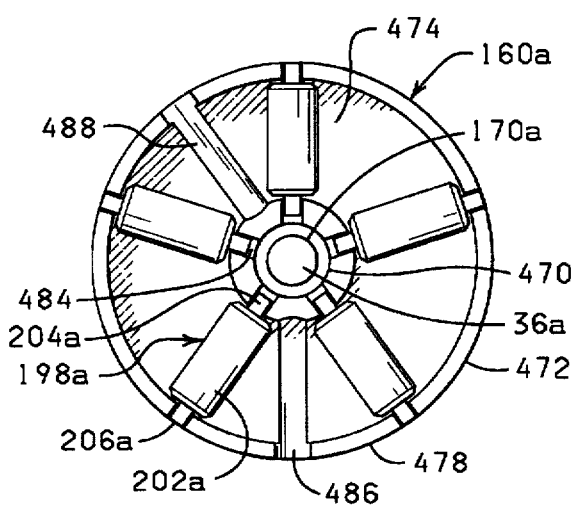

FIG. 31 is a top plan view of the modified rod support member and plurality of rods as shown in FIGS. 28–30.

Figure 32:
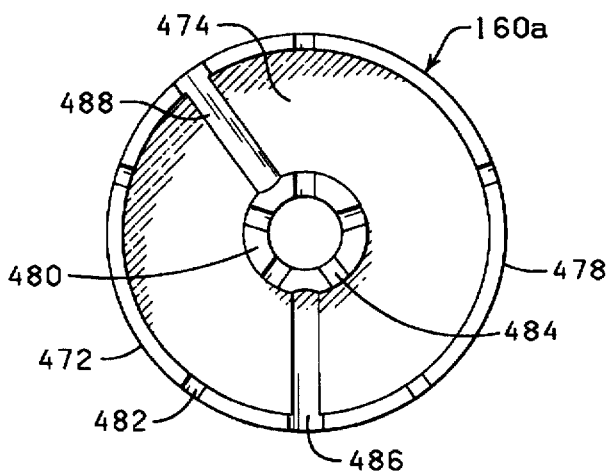

FIG. 32 is a top plan view of the modified rod support member of FIG. 31, but showing the modified rod support member without the plurality of rods therein.

Figure 33:
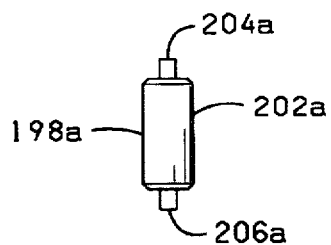

FIG. 33 is a side elevational view of one of the plurality of rods shown in FIG. 31.

Figure 34:
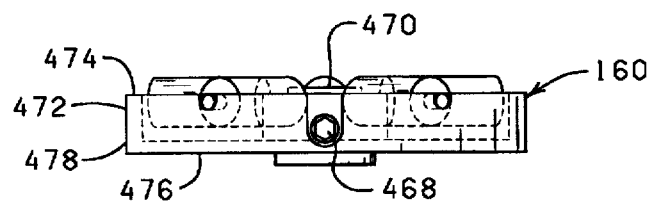

FIG. 34 is a side elevational view of the modified rod support member and plurality of rods of FIG. 31.

Figure 35:
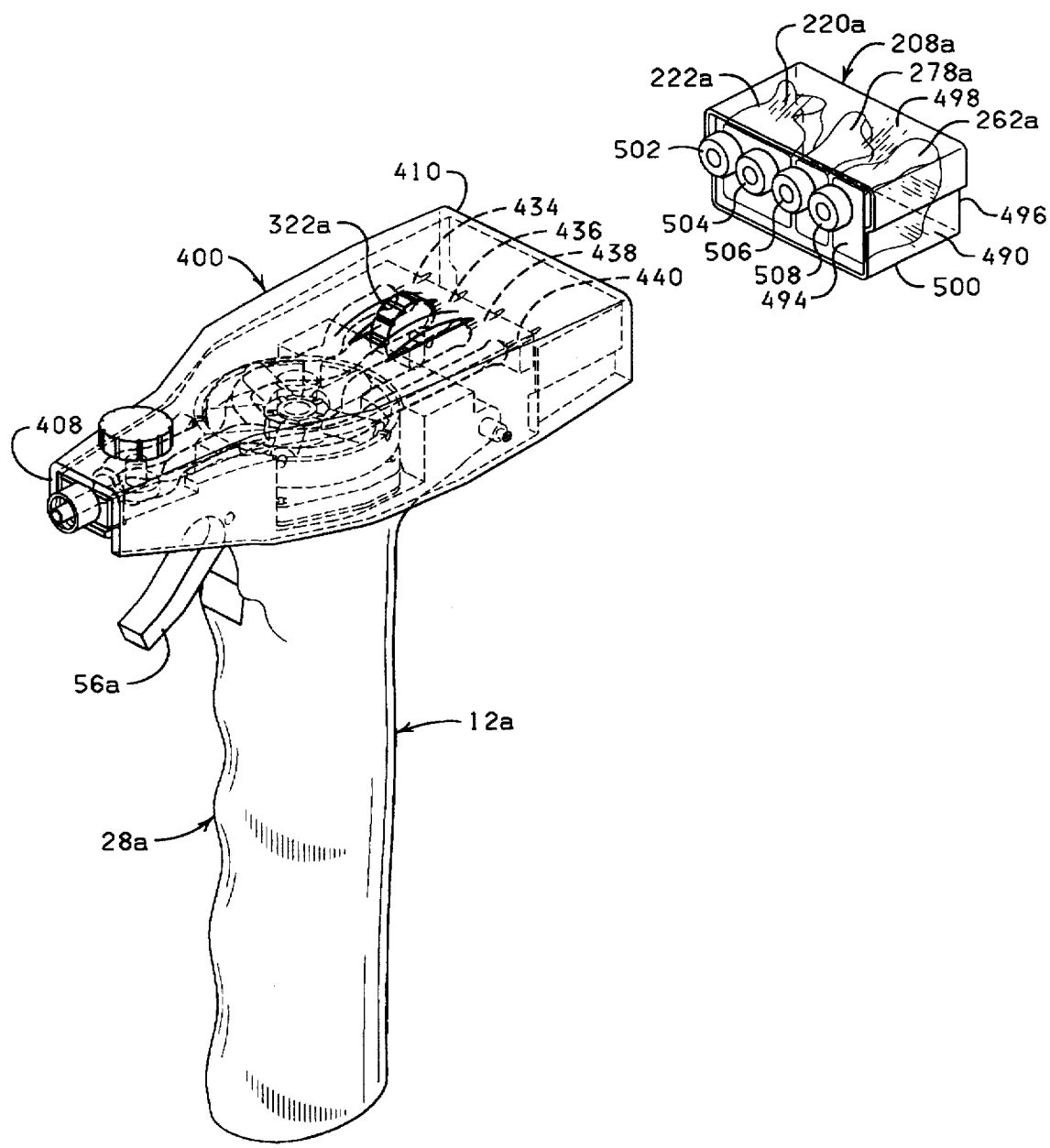

FIG. 35 is a perspective view of the modified biosample aspirator of FIG. 21, but showing the container compartment disengaged.

Figure 36:
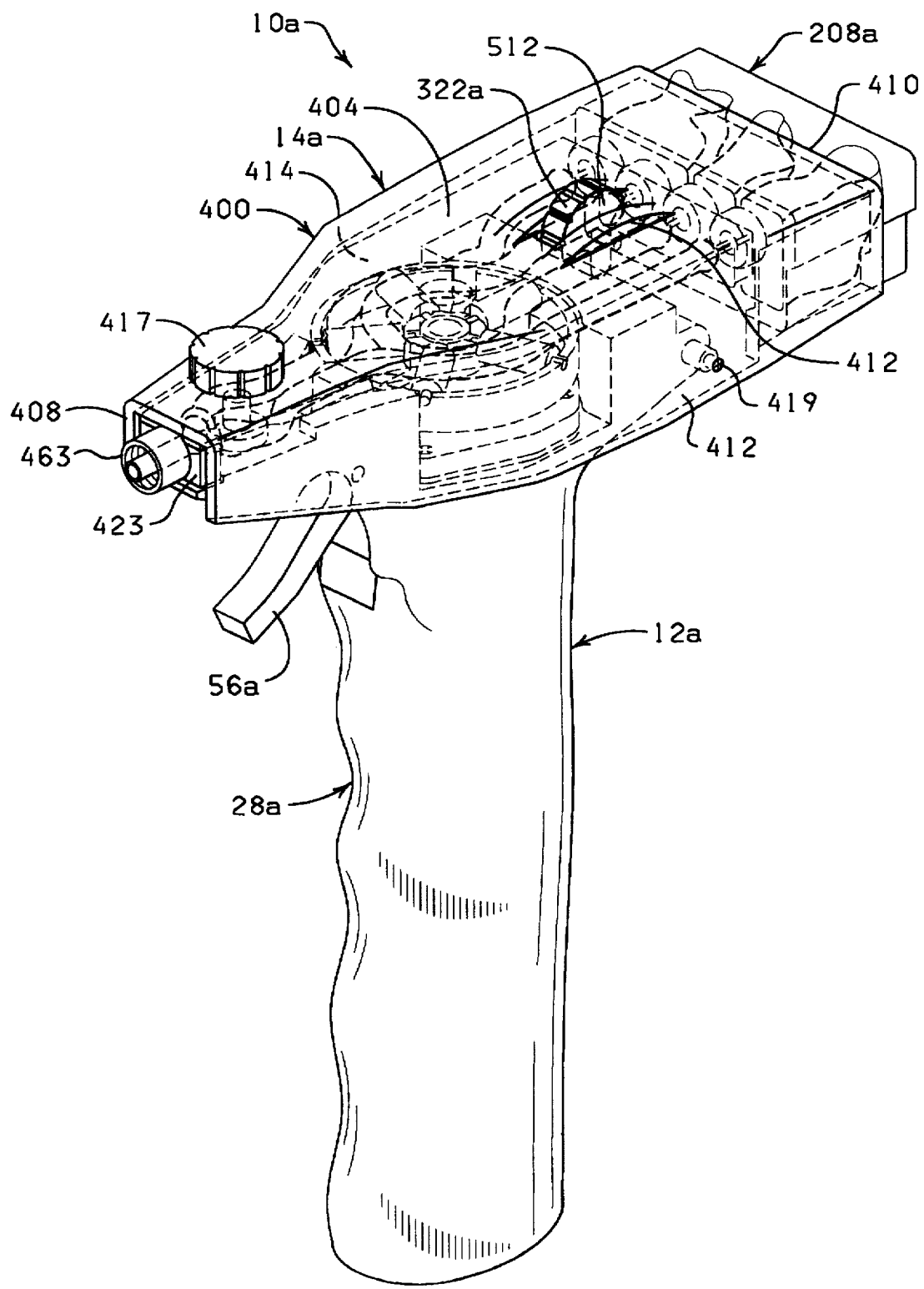

FIG. 36 is a perspective view of the modified biosample aspirator of FIGS. 21 and 35, but showing the container compartment in engagement with the card in the modified biosample aspirator.

DETAILED DESCRIPTION OF THE PREFERRED EMBODIMENTS

The Embodiments and Methods of FIGS. 1–20

The present invention comprises a fine-needle aspirator adapted for use in collecting a biosample such as fluid or tissue from a subject such as a human into a closed sterile system. The aspirator is adapted to be used with a needle having a first end and a second end with an opening therethrough and comprises a biosample collection system and a suction means.

The suction means generates and establishes a vacuum capable of continuous suction in the biosample collection system whereby a biosample received via the first end of the needle is movably transferred through the needle opening into the biosample collection system. The biosample collection system comprises a biosample collection area and a communicating means for establishing fluidic communication between the needle opening and the biosample collection area. The biosample collection area may be part of the communication means or may comprise a biosample container connected to the communication means having a collection space sized to receive at least one biosample.

Figure 1:
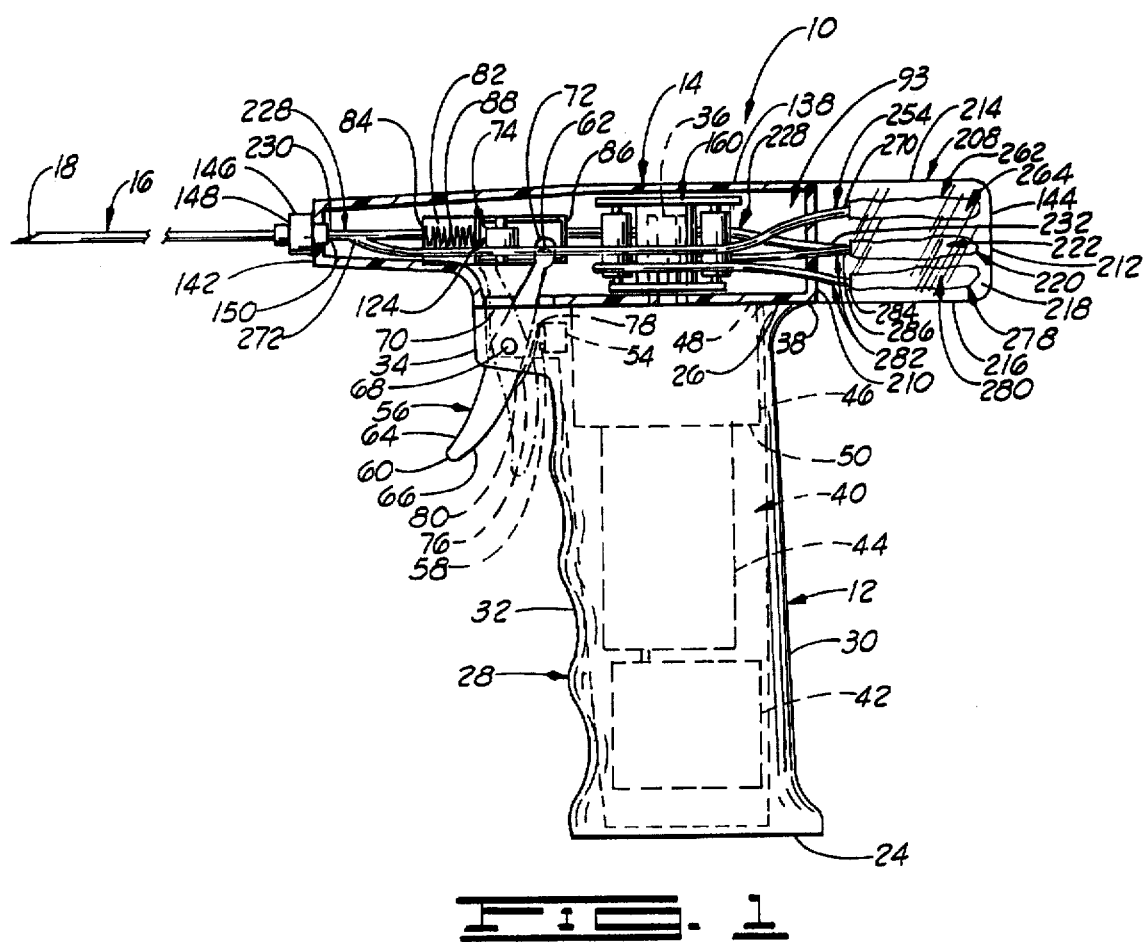
FIG. 1 is a side view in cross section of the biopsy gun constructed according to the present invention.

Referring to the drawings in detail, and particularly FIGS. 1-20, reference character 10 generally designates a biosample aspirator in accordance with the present invention. As shown in FIG. 1, the aspirator 10 comprises a handle housing generally designated by reference character 12 and a pump housing generally designated by reference character 14. A needle 16 having a first end 18 and a second end (not shown) with an opening (not shown) therethrough is secured to the pump housing 14 as described hereafter.

The handle housing 12 comprises a lower end 24 and an upper end 26 with a front surface 28 and back surface 30. The handle housing 12 is sized to be held by one hand and has a generally rounded or oval cross section. The handle housing front surface 28 has a grip area 32 shaped to be easily gripped by one hand while the handle housing back surface 30 is generally straight. The front surface 28 of the upper end 26 portion of the handle housing 12 extends a distance from the grip area 32 to form a tapered trigger attachment portion 34. The lower end 24 of the handle housing 12 is generally flat and may be adapted to be received in a recharging unit (not shown) capable of recharging the battery contained within the handle housing 12. The upper end 26 of the handle housing 12 has a shaft opening (not shown) through which a rotatable shaft 36 extends therethrough as described hereafter. The upper end 26 of the handle housing 12 secures the lower end 38 of the pump housing 14. The upper end 26 of the handle housing 12 is formed so that the pump housing 14 selectively snaps onto and off of the handle housing 12 removably securing same.

A housing component space 40 is formed inside the handle housing 12 and is sized to receive a battery 42, motor 44 and gear box 46. In one embodiment, a battery 42 is disposed near the lower end 24 portion of the handle housing 12 in the component space 40 and is operatively connected to a motor 44 positioned above the battery 42 as shown in FIG. 1 to provide electrical current thereto. Mounted on the motor 44 is a gear box 46 having a upper end 48 and a lower end 50. A rotatable shaft 36 extends a distance from the upper end 48 of the gear box 46 through a shaft opening (not shown) in the upper end 26 of the handle housing 12 and into the pump housing 14 through the pump housing shaft aperture 52 (FIG. 5). The battery, motor and gear box of the cordless screwdriver model #9018 made by Black and Decker of Shelton, Conn. may be used in accordance with the present invention.

Figure 9:
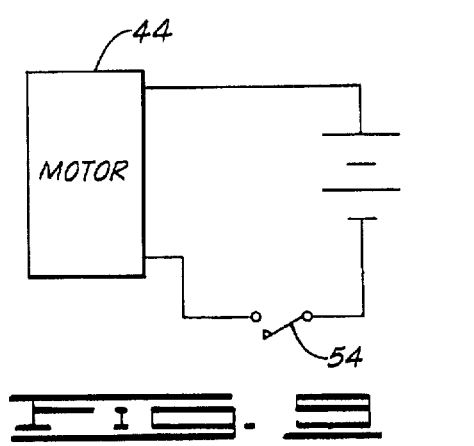
FIG. 9 is a schematic drawing of the switch of the present invention in the open position.
Figure 10:
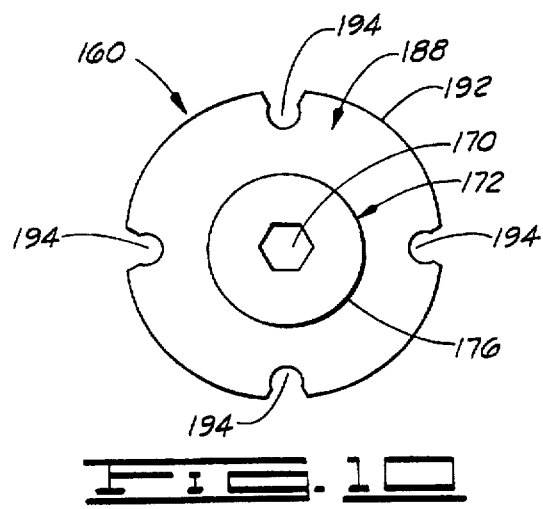
FIG. 10 is a bottom plan view of the rod support member.

The electrical current to the motor 44 is selectively provided by a microswitch 54 having an opened and a closed position interposed between the battery 42 and the motor 44 for establishing electrical continuity therebetween. When the microswitch 54 is in a closed position, electrical continuity between the battery 42 and the motor 44 is established and the motor 44 is in a driven or on condition. Electrical continuity between the motor 44 and the battery 42 is interrupted when the microswitch 54 is in the open position as schematically shown in FIG. 9.

The microswitch 54 is positioned in the handle housing component space 40 near the trigger 56. The microswitch 54 also comprises a microswitch button 58 disposed between the microswitch 54 and the trigger 56 so that the trigger 56, when pressed, can selectively contact the microswitch button 58. Contact of the microswitch button 58 by the trigger 56 conditions the microswitch 54 in the closed position.

The trigger 56 may be secured to either the handle housing 12 or the pump housing 14. In the embodiment shown in FIG. 1, the trigger 56 is pivotally secured to the trigger attachment portion 34 of the handle housing 12. The trigger 56 has a tapered lower end 60, an enlarged ball-shaped upper end 62, an inwardly curved finger surface 64 and an outwardly curved back surface 66. The trigger 56 is pivotally secured at about the middle of the trigger to the trigger attachment portion 34 of the handle housing 12 by a pin 68 through aligned pin holes (not shown) in the trigger attachment portion 34 of the handle housing 12 and the trigger 56. The upper end 62 portion of the trigger 56 is received in the handle housing component space 40 with the upper end of the trigger 56 extending through the lower end 38 of the pump housing 14 through the trigger aperture 70 (FIG. 5) with the upper end 62 of the trigger 56 positioned in the trigger tip opening 72 of the trigger slide 74 (FIG. 4) as described hereafter.

The trigger back surface 66 contacts the microswitch button 58 when the trigger finger surface 64 is pressed towards the front surface 28 of the handle housing 12. A trigger spring 76, having an upper end 78 and a lower end 80, is attached near the microswitch button 58 by the upper end 78 thereof. The lower end 80 thereof extends a distance from the microswitch 54, between the trigger back surface 66 and the microswitch 54 so that when the trigger 56 is pressed the trigger back surface 66 contacts the lower end 80 of the trigger spring 76 thereby compressing the trigger spring 76. When the trigger 56 is no longer pressed, the trigger spring 76 resiliently returns to the decompressed position thereby repositioning the trigger 56 in the off position.

Figure 13:
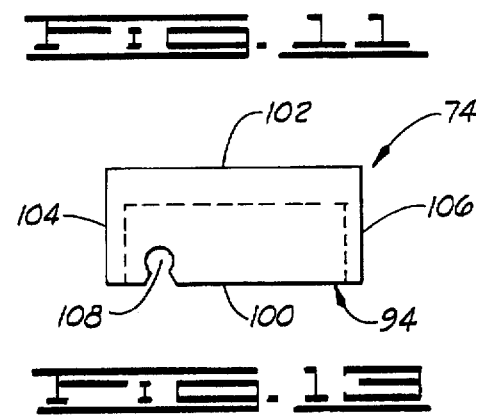
FIG. 13 is a top plan view of the control member guide.
Figure 14:
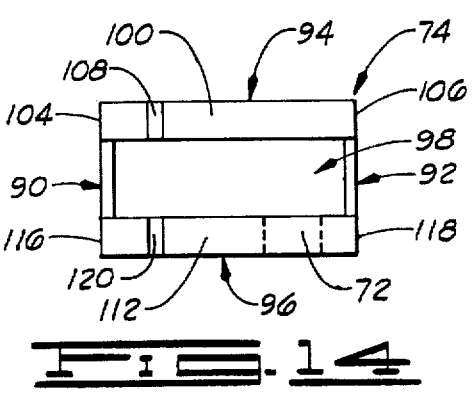
FIG. 14 is a side elevational view of the control member guide.
Figure 15:
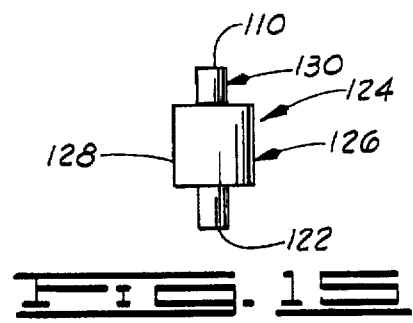
FIG. 15 is a side elevational view of the control member.

A trigger slide aperture 82 having a first end 84 and a second end 86 is formed in the pump housing component space 93 and sized to receive a trigger slide 74 with attached slide spring 88 in an extended position. Referring to FIGS. 13 and 14, the trigger slide 74 comprises a first end plate 90, a second end plate 92, a top plate 94, a bottom plate 96 and a back plate 98. The top plate has a front end 100, a back end 102, a first end 104 and a second end 106 and comprises a control member opening 108 near the first end 104 portion of the top plate 94 sized to secure the upper end 110 of the control member shaft shown in FIG. 15. The bottom plate 96 has a front end 112, a back end 114, a first end 116, and a second end 118 and comprises a control member opening 120 near the first end 116 portion of the bottom plate 96 sized to secure the lower end 122 control member shaft shown in FIG. 15. The control member openings 108 and 120 are aligned so that the control member, as described hereafter, secured therein is supported in an upright position.

As shown in FIGS. 1 and 4, the bottom plate 96 further comprises a trigger tip opening 72 which removably receives the trigger upper end 62. The top plate 94 and the bottom plate 96 are generally horizontally positioned with a back plate 98 secured therebetween at the back end 102 of the top plate 94 and the back end 114 of the bottom plate 96. A first end plate 84 and the second end plate 86 are in a generally vertical position. Referring to FIG. 14, the first end plate 90 secures the first end 104 of the top plate 94, the first end 116 of the bottom plate 96 and a portion of the back plate 98; the second end plate 92 secures the second end 106 of the top plate 94, the second end 118 of the bottom plate 96 and a portion of the back plate 98.

Figure 7:
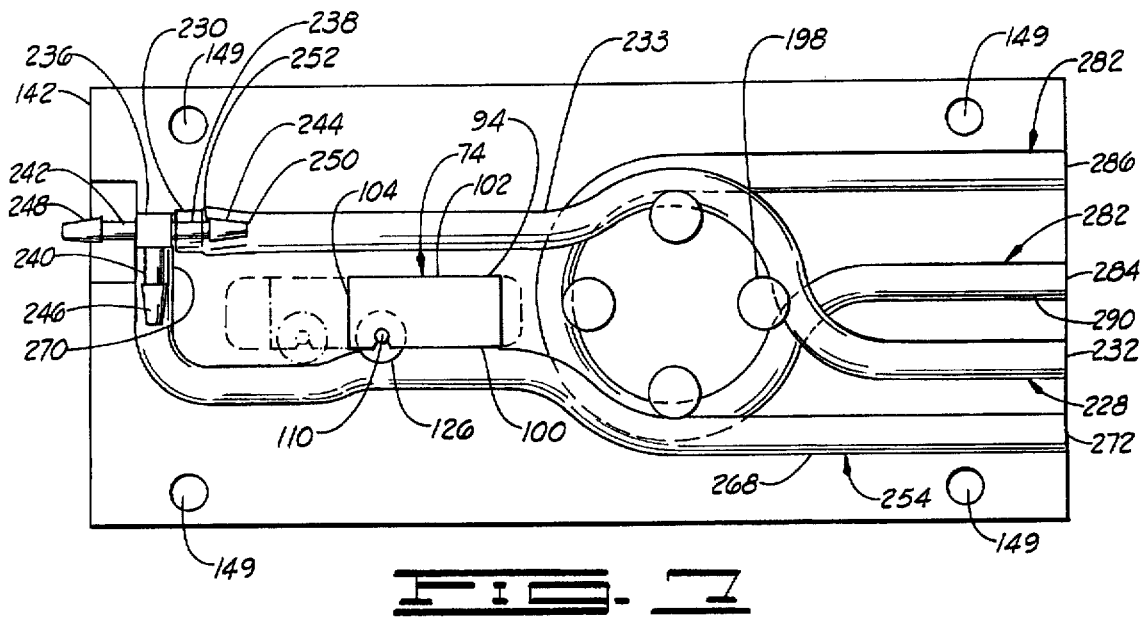
FIG. 7 is a horizontal cross sectional top plan view of a portion of the pump housing of the present invention without the slide spring.

The control member 124 (FIG. 15) comprises a cylinder 126 having an outer periphery 128 rollingly supported on a shaft 130 having an upper end 110 and a lower end 122 extending a distance from each end of the cylinder 126. The upper 110 and lower 122 ends of the control member shaft 130 are respectively secured in the control member opening 108 of the top plate 94 and the control member opening 122 in the bottom plate 96. The control member 124 secured in the trigger slide 74 is thereby selectively positioned to compress the flushing solution connector (interrupt position) or decompress the flushing solution connector (enable position) as shown in FIG. 7 and as described hereafter.

The slide spring 88 has a first end 132 secured to the trigger slide first end plate 90 and a second end 134 secured to the pump housing 14 adjacent to the first end 84 of the trigger slide aperture 82.

In operation, a finger presses the finger surface 64 of the lower end 60 of the trigger 56 towards the handle housing front surface 28 thereby contacting the trigger spring 76 and the micro-switch button 58 to establish the on position for the trigger 56. This moves the upper end 62 of the trigger 56 engaged in the trigger tip opening 72 of the trigger slide 74 in the opposite direction thereby compressing the slide spring 88. The control member 124, attached to the trigger slide 74, is thereby positioned so that the flushing solution connector 254 is decompressed and flushing substance may be aspirated therethrough as described hereafter. When the trigger 56 is no longer pressed by the operator, the trigger spring 76 decompresses returning the triggers slide 74 with attached control member 124 and trigger 56 to the original position. Since the microswitch button 58 is no longer contacted, the microswitch 54 is in the open position conditioning the motor in an off position.

The pump housing 14 comprises an upper surface 138, a lower surface 38, a first end 142 and a second end 144. A pump housing component space 93 is formed within the pump housing 14 intersecting the first end 142 and the second end 144. The first end 142 of the pump housing 14 has a needle receiving opening (not shown) to receive a needle 16.

In the embodiment shown in FIG. 1, an annular needle receiving adaptor 146 has a first end 148 and a second end 150 with an opening therethrough (not shown). The adaptor second end 150 portion is secured in the opening of the pump housing first end 142 and secures either a tubing first end 230 as shown in FIG. 1 or a tubular projection 242 with attached shoulder 248 as shown in FIG. 7 and described hereafter. The adaptor first end 148 removably secures a luer lock needle attachment (not shown) secured to the second end of the needle 16.

Figure 2:
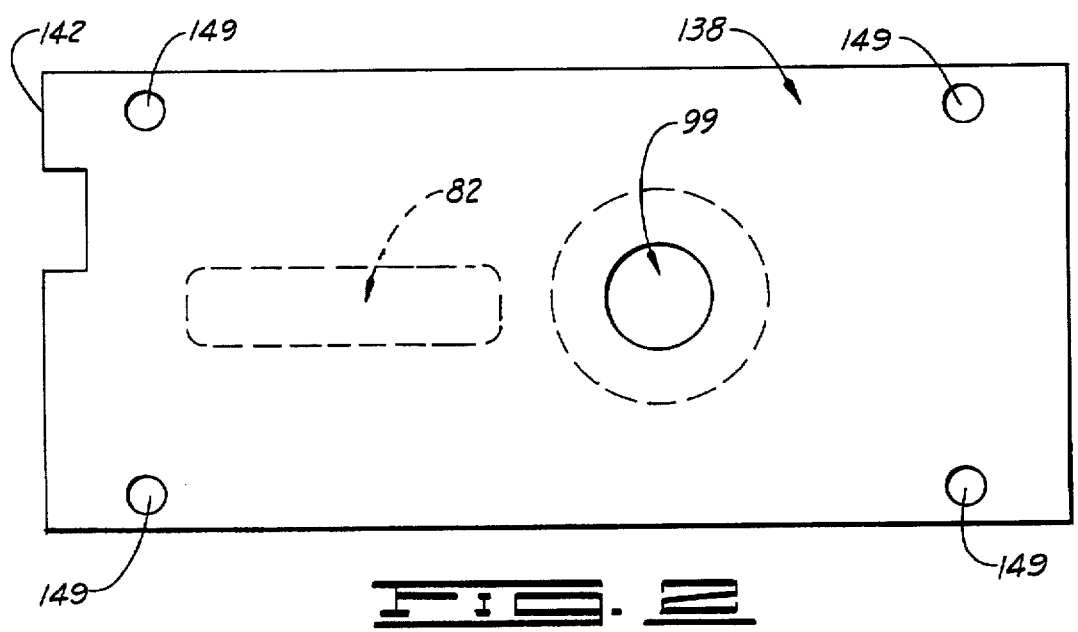
Figure 6:
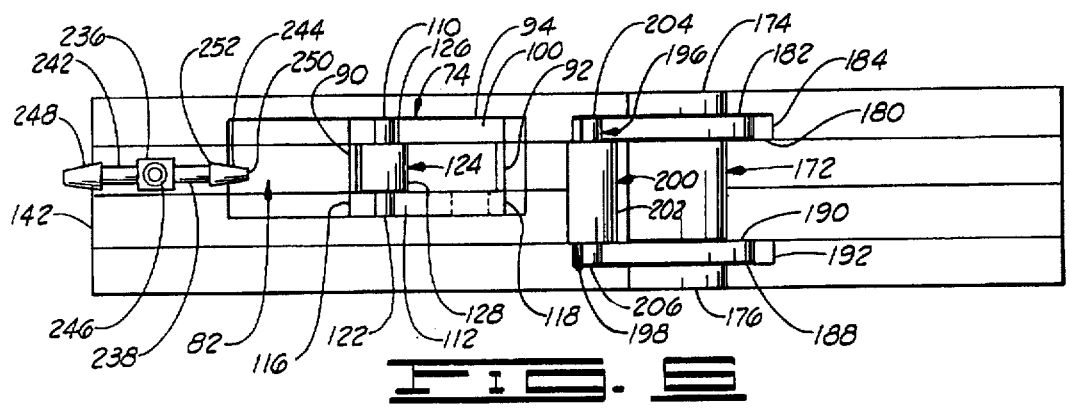
FIG. 6 is a vertical cross sectional view of a portion of the pump housing of the present without the connectors and the slide spring.

FIGS. 2 through 5 show the pump housing 14 in horizontal block cross sections as used in the manufacturing process of one embodiment. These same sections may be shaped to conform to the outer dimensions of the pump housing shown in FIG. 1. FIG. 5 represents the lowest section upon which respectively the sections in FIGS. 4, 3 and 2 are mounted. FIG. 5 shows the pump housing shaft aperture 52 which receives the shaft 36 from the gearbox 46 and the trigger aperture 70 which receives the upper end 62 of the trigger 56. FIG. 2 shows the support post opening 99 which receives the upper end 174 of the support post 172 as described hereafter.

After the appropriate components as described hereafter have been disposed in the pump components space 93, a bolt (not shown) secured in each of the aligned bolt apertures 149 secures the pump housing sections together. The pump housing sections form a pump housing component space 93 which intersects the first end 142 and the second end 144 of the pump housing 14.

A portion of the pump housing component space 93 comprises an eccentrically formed bowl-like rod support member space 158 which receives the rod support member 160 and comprises a continuous first front wall 162 (FIG. 3) and second front wall 164 (FIG. 4), a continuous first back wall 166 (FIG. 3) and second back wall 168 (FIG. 4) and a side wall 169. The space between the outer periphery 192 of the rods 198 of the rod support member 160 and the walls of the rod support member space 158 dictate whether the connectors disposed in that space are contacted by the rod support member 160, i.e., if that space is smaller than the diameter of the connectors the rods of the rod support member will compressingly engage the connectors. This engagement creates a vacuum in the connectors. Thus the shape of the rod support member space selectively controls the amount of contact between the connectors and the rods and therefore the degree of vacuum created in the connectors.

The pump housing component space 93 further comprises a first biosample canal 258 and a second flushing canal 256 that intersect at the first end 142 portion of the pump housing 14 and lead to the rod support member space 158 in about the middle of the pump housing 14. A first flushing canal 276, a second biosample canal 260, an upper additive canal 312 and a lower additive canal 300 lead from the rod support member space 158 to the second end 144 portion of the pump housing 14. The canals 256, 258, 260, 276, 312 and 300 are sized to receive a connector therein as described hereafter.

As previously described, a shaft 36 from the gear box 46 extends into the rod support member space 158 and is engagingly received in the support post aperture 170 of the rod support member 160 (FIG. 11) so that as the shaft 36 rotates, the rod support member 160 rotates. The rod support member 160 comprises a support post 172 having an upper end 174 and a lower end 176. The lower end 176 of the support post 172 has an aperture 170 (FIG. 10) sized to engagingly receive the shaft 36. The shaft 36 is hexagonal and sized slightly smaller than the hexagonally shaped aperture 170 in the support post 172.

Figure 11:
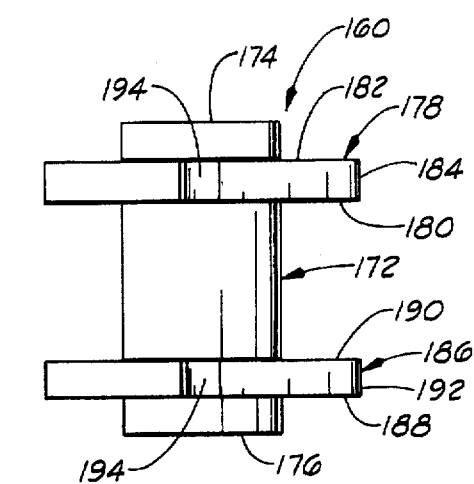
FIG. 11 is an elevational side view of the rod support member.

Referring to FIG. 11, the rod support member 160 further comprises an annular upper rod support 178 secured to the upper end 174 portion of the support post 172 having a lower face 180, an upper face 182 and an outer periphery 184, and an annular lower rod support 186 secured to the lower end 176 portion of the support post 172 having a lower face 188, an upper face 190 and an outer periphery 192. The upper rod support 178 and lower rod support 186 include a plurality of rod receiving slots 194 spaced a distance around the periphery 184 and 192 of the rod supports 178 and 186. The slots 194 are shaped and positioned so that a rod shaft 196, as described hereafter, can snap into the slots and be securely supported in an upright position around the rod support member 160.

Figure 12:
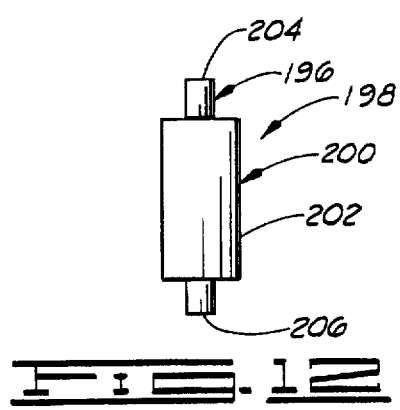
FIG. 12 is an elevational side view of a rod.

As shown in FIG. 12, the rod 198 comprises a rod cylinder 200 having an outer periphery 202 rollingly supported on a rod shaft 196 wherein the shaft has an upper end 204 and a lower end 206 which extends a distance from opposite ends of the rod cylinder 200. The upper end 204 of the rod shaft is sized to snap into rod receiving slot 194 in the periphery 202 of the upper rod support 178; the lower end 206 of the rod shaft 196 is sized to snap into the rod receiving slot 194 in the lower rod support 186 thereby securing the rod 198 in an upright position in the rod support member 160. Secured in this manner, the outer periphery 202 of the rod cylinder 200 extends a distance from the rod support member 160 to rollingly engage a portion of the connectors as described hereafter.

In one embodiment, a peristaltic pump comprising four rods 198 secured at equispaced distances in the foregoing manner in the rod support member 160 providing a circular configuration of rotatable rods 198 is utilized in accordance with the present invention. When the motor 44 is in the on position, the shaft 36 rotates which rotates the rod support member 160 having the rods 198 secured thereto. Selected connectors, as described hereafter, are alternately compressed by the rods 198 in a peristaltic movement when the outer periphery 192 of each rod 198 rolls along the connectors thereby compressing the connectors. This engagement of the connectors by the rods 198 creates a vacuum in the connectors and attached needle 16.

Instead of the peristaltic pump described in the foregoing, the present invention may use any other type of pump which appropriately provides the necessary vacuum action in the biosample collection system. FIG. 19 shows an embodiment of the present invention which utilizes a piston pump 209 driven by a motor source. The piston pump 209 produces a vacuum in the biosample collection system and the needle 215. The biosample collection system comprises a biosample container 211, biosample connector 213, additive connector 217, additive container 219, flushing connector 254 and flushing container 223.

At least one container is disposed in the pump housing component space 93 near the second end 144 of the pump housing 14. As shown in FIG. 1, an embodiment of the second end 144 of the pump housing 14 comprises a clear plastic container compartment 208 having a first end 210, a second end 212, an upper surface 214, a lower surface 216 and a container component space 218 formed therein which is part of the pump housing component space 93 and is sized to receive one or more containers. The container compartment 208 is secured to the second end 144 portion the pump housing 14 so that the upper 214 and lower surface 216 of the container compartment 208 are about flush respectively with the upper 138 and lower 38 surfaces of the second end 144 portion of the pump housing 14 and has the same general cross section as the second end 144 portion of the pump housing 14.

A biosample container 220 having a collection space 222 sized to receive at least one biosample is disposed in the second end 144 portion of the pump housing component space 93 and, most frequently, in the container component space 218. The biosample container 220 must be able to withstand the suction pressure exerted by the pump. In one embodiment, the biosample container 220 is an elastomeric sack. In another embodiment, the biosample container 220 is a molded flexible polyurethane compartment.

The collection space 222 of the biosample container 220 is in communication with the second end of the needle 16 so that a biosample collected by the needle 16 may be deposited in the collection space 222 of the biosample container 220. This communication is established by a biosample connector 228 having a first end 230, a second end 232, an outer periphery 233 and an opening (not shown) therethrough. In a one embodiment, the biosample connector 228 is elastomeric tubing.

The second end 232 of the biosample connector 228 is secured to a biosample container 220 so that the collection space 222 hereof is in communication with the opening in the biosample connector 228. The first end 230 of the biosample connector 228 is connected to the second end of the needle 16. As shown in FIG. 7, this connection may be accomplished by a conduit 236 having a first 238, second 240 and third 242 tubular projection extending therefrom thereby forming a T tubing. The terminal ends of the first, second, and third tubular projections have secured thereto respectively a first 244, second 246 and third 248 annular shoulder, having a first end 250 and a second end 252 wherein the second end 252 faces the conduit 236. There is an increase in size of the shoulder towards the conduit whereby the first end 250 of the shoulder has a smaller outside diameter than the second end 252 of the shoulder. The biosample connector 228 is sized to slide easily over the first end 250 of the shoulder 244 but must be forced over the second end 252 of the shoulder thereby securing the connector 228 to the tubular projection 238.

As previously described the second end of the needle 16 is in communication with the opening of the third shoulder 248 thereby establishing fluid communication between the first end 18 of the needle 16 and the collection space 222 in the biosample container 224. In one embodiment, a flushing connector 254 is secured to the second shoulder 246 in the same manner as the first shoulder 244 to provide fluidic communication for the flushing substance to the biosample connector 228 as described hereafter. Another embodiment shown in FIG. 1 eliminates the need for the T tubing by fusing the flushing connector 254 to the biosample connector.

The first end 230 portion of the biosample connector 228 is positioned in the first biosample canal 258 of the pump housing component space 93 (FIG. 3) and follows the first back wall 166 of the rod support member component space 158. The second end 232 portion of the biosample connector 228 is positioned in the second biosample canal 260 which leads to the pump housing second end 144 portion containing the biosample container 220. The space between the first back wall 166 of the rod support member space 158 and the rods 198 is less than the diameter of the biosample connector 228 so that positioning the biosample connector 228 in this space permits the rotating rods 198 of the rod support member 160 to compressingly engage the biosample connector 228 as in FIG. 7 thereby creating a suction therein.

Figure 8:
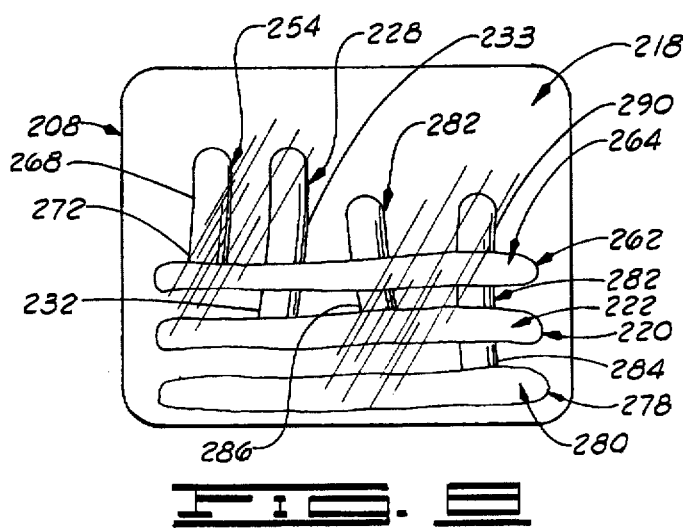
FIG. 8 is an elevational view of the second end of the pump housing of the present invention showing the clear plastic container compartment with connectors attached to the containers.

As shown in FIGS. 1 and 8, a flushing container 262 is positioned in the container compartment component space 218 and has a flushing substance space 264 formed therein sized to retain an effective amount of a flushing substance such as sterile normal saline solution. The flushing container 262 is frequently made from the same material as the biosample container 220.

A flushing connector 254 having an outer periphery 268, a first end 270 and a second end 272 with a connector opening (not shown) formed therethrough is shown in FIGS. 1 and 7. The second end 272 of the flushing connector 254 is connected to the flushing container 262 so that the flushing connector opening is in fluid communication with the flushing substance contained in the flushing container 262. In the embodiment shown in FIG. 7, the first end 270 of the flushing connector 254 is secured to the second tubular projection 240 as previously described so that the flushing connector opening is in fluid communication with the biosample connector opening (not shown). In the embodiment shown in FIG. 1 the first end 270 of the flushing connector 254 is fused at approximately a 30° angle to the biosample connector 228 to establish fluidic communication therebetween. Usually, the flushing connector is elastomeric tubing.

The second end 272 portion of flushing connector 254 is positioned in the first flushing canal 276 and contactingly follows the first front wall 162 to the second flushing canal 256. The space between the first front wall 162 and the outer periphery 202 of the rod cylinders 200 is larger than the diameter of the flushing connector 254 so the flushing connector 254 is not engaged by the rods 198 (FIG. 7). The flushing substance within the flushing container 262 is aspirated through the flushing connector opening by the suction created in the biosample connector 228 in communication therewith. The flow of the flushing substance is interrupted by selectively compressing the flushing connector 254 with the outer periphery 128 of the control member cylinder 126 as shown in FIG. 7 and as previously described.

A third container may be disposed in the second end 144 portion of the pump housing component space 93 which contains an additive. The additive container 278 comprises an additive space 280 formed therein sized to retain an effective amount of additive and is often made from the same material as the biosample container 220. The additive container 278 is in communication with an additive connector 282 having a first end 284 and a second end 286 with an opening (not shown) therethrough and an outer periphery 290. Usually, the additive connector is elastomeric tubing.

The first end 284 of the additive connector 282 is secured to the additive container 278 and the second end 286 of the connector 282 is secured to the biosample container 220 or a portion of the biosample connector 228 near the biosample container 220 so that the additive is in communication with the collection space 222 of the biosample container 220. The additive does not enter the biosample connector 228 in a manner which could inadvertently contaminate the biosite with additive.

The first end 284 portion of the additive connector 282 is positioned in the lower additive canal 300 (FIG. 4.) and follows the second front wall 164, the side wall 169 and the second back wall 168 of the rod support member space 158 and into the upper additive canal 312 which leads to the biosample container 220. The space between the rods 198 and the walls of the rod support member space 158 is smaller than the diameter of the additive connector 282 so that the rotating rods 198 contact the additive connector 282 as shown in FIG. 7 creating a vacuum therein.

Referring to FIG. 20, the flow of the additive through the additive connector 282 can be regulated by an additive regulator generally designated by the numeral 283 which selectively compresses at least a portion of the additive connector 282. A ball 314 is disposed in the pump housing component space 93 near the upper additive canal 312 so that the ball compresses the additive connector 282. Between the ball 314 and the inside wall of the pump housing 316, usually in a recessed area, is disposed a ball spring 318. A ball rod 320 is secured at one end to the ball 314 and extends a distance from the pump housing 14 at the opposite end. An additive button 322 is secured to the end of the ball rod 320 which extends from the pump housing 316. When the additive is desired in the biosample container 220, the additive button 322 is pressed which extends the ball rod 320 thereby displacing the ball 314 from the compressed additive connector 282 which permits the flow of the additive therethrough. When the additive button 322 is no longer pressed the ball spring 318 resiliently returns to a decompressed positioned which pushes the ball onto the additive connector 282 compressing same.

As previously described, a commercially available needle may be used with the aspirator of the present invention. Alternately, the following needles may be utilized.

The flushing needle shown in FIG. 16 and generally designated by the numeral 324, comprises a first shaft 325 having a first end 326 capable of cutting and receiving a biosample, a second end 328 attachable to a needle receiving member 329 such as the aspirator of the present invention, a duct 330 having a first end 331 and a second end 333 intersecting the first 326 and the second ends 328 of the first shaft 325. The first shaft 325 is capable of receiving an effective amount of flushing substance such as sterile normal saline solution in the first end 331 portion of the duct 330. In one embodiment flushing substance is supplied to the first end 331 portion of the duct 330 by telescoping a second shaft 335 over the first shaft 325. The second shaft 335 comprises a first end 337 and a second end 339 secured to the first shaft 325 and a flushing substance space 341 formed between the first end 336 and the second end 339 of the second shaft 335. Flushing substance received by the flushing substance space 341 is received in the first end 331 portion of the duct 330 via a port 332 in the first end portion of the first shaft 325.

FIG. 16 shows a flushing solution reservoir attached to a second shaft port 338 positioned near the second end portion 339 of the second shaft 335; a valve 336 regulates the flow of flushing substance therebetween. The flushing solution is received in the flushing substance space 341 which is then received in the first end 331 portion of the duct 330 via port 332. A portion of the flushing solution is received at the biosite from the duct 330. A biosample is received by the first end 331 of the duct 330 and the flushing solution aids in the delivery of the biosample to the second end 333 thereof. Providing flushing substance to the first end portion of the duct and the biosite aids in obtaining and transferring biosamples from the biosite to a needle receiving member 329.

The obturator needle shown in FIG. 17 and generally designated by the numeral 340, comprises a shaft 343 having first end 342 capable of cutting and receiving a biosample, a second end 344 attachable to a needle receiving member 329 such as the aspirator of the present invention and an opening 346 intersecting the first end 342 and the second end 344 of the shaft 343. An obturator 348 having a first end 350 and a second end 352 is disposed in the opening 346 so that the obturator first end 350 blocks the opening of the first end 342 of the shaft 343. The opening 346 near the first end 342 of the shaft 343 is tapered and sized slightly larger that the diameter of the obturator 348. The remainder of the opening 346 is larger and sized to receive the obturator 348 and a biosample received by the first end 342 of the shaft 340. The second end 352 of the obturator 354 is attached to a means for withdrawing the obturator 354 a distance from the shaft first end 342 past the tapered portion of the opening 346 so that a biosample can be received by the needle first end 342 of the shaft 343. The withdrawing means is shown as an obturator trigger 354 in FIG. 17. The obturator needle 340 is used when several layers of tissue must be punctured before reaching the biosite. The obturator 348 prevents obtaining unwanted tissue samples until the first end of the needle is positioned at the biosite.

The flange needle shown in FIG. 18 and generally designated by the numeral 356 comprises a shaft 357 having a first end 358 capable of cutting and receiving a biosample, a second end 360 attachable to a needle receiving member 329 such as the aspirator of the present invention, an opening (not shown) intersecting the first 358 and the second 360 ends and an outer periphery 364. A flange member 366 is secured to the outer periphery 364 at a selected position in order to prevent further insertion of the needle 356 into a biosite. In operation, the first end 358 of the shaft 357 is inserted into the biosite such as a prostate gland. The flange member 366 acts as a guide to the operator to determine how far the shaft 357 has been inserted, and prevents a further insertion of the shaft 357 into an area past the prostate gland which could recover a biosample from an unintended biosite. The flange member 366 is usually made from the same material as the needle 356 and may be any shape which is large enough to form a stop surface in order to prevent inadvertent insertion into the patient. In one embodiment for use in prostate gland, the flange member 366 is positioned 1.5 inches from the first end 358 of the shaft 357.

In one operation, the first end 18 of the needle 16 is positioned at the desired biosite such as a prostate gland. The first end 18 of the needle 16 cuttingly engages the prostate gland thereby receiving a tissue biosample in the opening of the first end thereof. The trigger 56 is pressed which activates the pump thereby establishing a vacuum capable of continuous vacuum directly in the biosample connector 228 and indirectly in the needle opening. The biosample is aspirated through the needle opening, through the biosample connector 228 and into the collection space 222 in the biosample container 220.

Pressing the trigger 56 moves the control member 124 thereby permitting the flushing substance to be aspirated through the flushing connector 254 by the suction created in the biosample connector 228 by the pump. The flushing substance is delivered to the biosample connector 228 and aids in the delivery of the biosample to the collection space 222 by flushing the biosample into same.

When the trigger 56 is pressed by the operator, the pump creates a suction in the additive connector 282. The additive button 322 is pressed thereby decompressing the additive connector 282 which permits the transfer of the additive to the biosample container. The additive may be any agent which aids in preserving, treating or analyzing the biosample. The present invention is especially useful if the additive or additives can identify a condition in the biosample which aids in the immediate diagnosis of the patient. This would eliminate the time and expense of the biosample being analyzed in the laboratory or for the pathologist to be present in the operating room.

After the first biosample is delivered to the collection space 222, multiple biosamples may be obtained by repositioning the first end 18 of the needle 16 to obtain the next desired biosample and repeating the previously described procedure. After the desired biosample or biosamples have been obtained, the trigger is returned to the off position and the aspirator withdrawn from the biosite. The pump housing 14 is snapped off and sent to the laboratory for appropriate analysis of the biosample or the biosample is viewed through the clear plastic container compartment for the appropriate response. A new pump housing 14 is snapped on the handle housing 12 to obtain the next biosample.

In the laboratory the pump housing 14 containing the biosamples is snapped onto a handle housing 12 having a reverse motor position. The reverse motor position is engaged and the biosamples are aspirated from the biosample container 220, through the biosample connector 228 and needle 16 and into a container for analysis. Thus laboratory personnel need never touch the biosample.

The Embodiments and Methods of FIGS. 21–36

Referring to FIGS. 21–36, and particularly to FIGS. 21–27, reference character 10a generally designates a modified biosample aspirator identical to the biosample aspirator shown in FIGS. 1–20 and described in detail previously, except that the pump housing 14a comprises an upper surface 138a which comprises a hinged lid 400, the lower surface 38a of the pump housing 14a comprises a modified rod support member 160a which is oriented horizontally, and a plurality of rods 198a (only one of the plurality of rods being designated 198a) which rotate horizontally. A portion of the pump housing component space 93a is contained within the hinged lid 400, and is modified to permit a card 402 is be inserted therein, the card comprising the biosample connector 228a, the flushing connector 254a, and the additive connector 282a. Connected separately to the card 402 is a modified container compartment 208a. The modified container compartment 208a is a separate unit which may be connected and disconnected from the card 402 and the biosample aspirator 10a. And, a new reversing switch 403 is contained within the handle housing 12a, to permit the pump to rotate the modified rod support member 160a in the opposite (counter clockwise) direction. Additional modifications will be described below.

Referring to FIGS. 22 and 28, the hinged lid 400 further comprises an upper surface 404, a lower surface 406, a first end 408, second end 410, a first side 412 and a second side 414. A portion of the pump housing component space 93a contained within the hinged lid 400 forms a card space 416, for insertion of a card 402, which will explained in detail below.

The hinged lid 400 further has a connecting element 417 which is attached to the upper surface 404 of the hinged lid 400, near the first end 408. "Connecting element" as used herein means any component, such a screw (FIGS. 21, 22 and 28), a hinge, or any other device known to those of ordinary skill in the art which connects or firmly engages the hinged lid 400 to the modified lower surface 38a of the modified pump housing 14a, but which is capable of easy release by an operator. It will be appreciated that the connecting element 417 may connectingly engage an engaging element 418 in order to hold the hinged lid 400 in a closed engagement against the pump housing 14a, and in order to hold the card 402 in an engagement against the modified rod support member and plurality of rods 198a therein, as is discussed and described in further detail below. "Engaging element" as used herein is any nut or other device known in the art which would permit a connecting element 417, as described herein, to be held in a connecting yet releasable engagement therewith.

First and second hinges 419 and 420, respectively, are connected to the hinged lid 400. First hinge 419 connects to the first side 412 of the hinged lid 400 and second hinge 420 connects to the second side 414 of the hinged lid 400. The first and second hinges 419 and 420, respectively, hingeably connect the hinged lid 400 to the lower surface 38a of the pump housing 14a near the modified second end 144a thereof, as illustrated in FIGS. 22 and 28. The hinged lid 400 further comprises, on the lower surface 406 thereof, a cylindrical stop 421, which spaces the hinged lid a distance from the lower surface 38a of the pump housing 14a. The cylindrical stop 421 extends through a corresponding aperture in the card 402, thereby ensuring that the card 402 does not slide within the card space 416 when the card 402 is inserted into the card space 416, as will be described herein in further detail.

The hinged lid 400 hingeably swings opens to expose the pump housing component space 93a, as shown in FIGS. 28–30. A plurality of slots 422 (only one slot designated by the numeral 422) are located on the upper surface 404 of the hinged lid 400. A modified additive button 322a is provided in one of the plurality of slots 422. The modified additive button 322a has a hinging rod extending therethrough and through at least two of the plurality of slots 422, thereby hingeably connecting the modified additive button 322a to the hinged lid. The modified additive button 322a is capable of being operated by an operator's thumb, and will be described in further detail below.

Referring now to FIGS. 21, 26, 29-30, the card 402 is positioned in the card space 416 which is formed in the portion of the pump housing component space 93a contained within the hinged lid 400. The card 402 comprises a first end 423, a second end 424, an upper surface 426, a lower surface 428, and an outer periphery 430.

Turning to FIG. 26, which illustrates the upper surface 426 of the card 402, the card 402 has connected to the second end 424 thereof via an elongated bar 432. A first needle 434, a second needle 436, a third needle 438 and a fourth needle 440 are connected to the elongated bar 432. Each of the first, second, third and fourth needles 434, 436, 438 and 440, respectively, have first ends 442, 444, 446, and 448, respectively. Each of the first, second, third and fourth needles 434, 436, 438 and 440, respectively, also have second ends 450, 452, 454, and 456, respectively. The first ends 442, 444, 446 and 448 of the first, second, third and fourth needles 434, 436, 438 and 440 each connect to a needle connector 457 (only one of the plurality of needle connectors designated 457). Each of the plurality of needle connectors 457 is at least partially disposed in the elongated bar 432, as are at least a portion of the first, second, third and fourth needles 434, 436, 438, 440, respectively. The respective second ends 450, 452, 454, and 456 of the first, second, third and fourth needles 434, 436, 438 and 440, respectively, are sharply pointed, although it will be appreciated that the second ends 450, 452, 454 and 456 may instead be blunt as long as the needles operate in the manner described herein. It will be understood that each of the first, second, third and fourth needles 434, 436, 438, and 440, respectively, have an opening therethrough.

The oval slot 458 is positioned in the card 402 near the second needle 436, and over a portion of the additive connector 282a near the second end 286a of the additive connector 282a, as will be described in detail below. A first aperture 460 is disposed, generally, in the center of the card 402, through which the cylindrical stop 421 will be inserted when the card 402 is inserted in the card space 416 as will be described in below in further detail.

At the first end 423 of the card 402 on the upper surface 426 is a first section 462. Connected to the first section 462 is a needle adapter. A short distance from the first end 423 of the card 402 is a second aperture 464, which permits at least a portion of the connecting element 417 to extend therethrough to engage the engaging element 418 when the card 402 is disposed in the card space 416, as shown in FIGS. 21 and 30, thereby connecting the hinged lid 400 to the lower surface 36a of the pump housing 14a, such engagement causing a pressing engagement of the rod support member 160a and the plurality of rods 198a therein against the biosample connector 228a, the flushing connector 254a, and the additive connector 282a.

Referring now to FIG. 27, which shows the lower surface 428 of the card 402 and the biosample connector 228a, the flushing connector 254a, and the additive connector 282a connected thereto. Connected to the first end 230a of the biosample connector 228a is a modified conduit 236a having first, second, and third tubular projections 238a, 240a and 242a which are modified to form a Y tubing, the first end 230a of the biosample connector 228a being connected to the first tubular projection 238a. The first, second and third tubular projections 238a, 240a and 242a, respectively, may optionally each have an angular shoulder (previously described), or, alternatively, each may be without an angular shoulder (as shown in FIG. 27). The second aperture 464, as previously described, is located near the first end 423 of the card 402, generally near the Y tubing conduit 236a.

A needle 16a (not shown), as previously described herein, is connected to the third tubular projection 242a of the Y tubing conduit 236a and the first end 230a of the biosample connector 228a (via a needle adapter 463, such as, for example but not by way of limitation, a luer lock or any other device known in the art, which in turn is connected to the conduit 236a, which is connected to the biosample connector 228a as previously described) for moving a biosample from the needle 16a to the biosample container 220a, as will be described in further detail below. The biosample connector 228a forms a small semi-circular loop around the second aperture, and generally runs down the center of the lower surface 428 of the card 402 and parallel with respect to the flushing connector 254a for a distance, then forms a larger semi-circular loop around the additive connector 282a (which loops around the cylindrical stop 421) near the outer periphery 430 of the card 402, and the second end 232a of the biosample connector 228a connects to the first needle 434 via the directly adjacent needle connector 457.

On the lower surface 428 of the card 402, a flushing connector 254a is connected to the second tubular projection 240a of the conduit 236a, via the first end 270a of the flushing connector 254a, for utilizing a flushing solution to move a biosample through the biosample connector 228a and into biosample container 220a in the container compartment 208a, as described in detail herein. The flushing connector 254a forms a small semi-circular loop around the second aperture 464, and generally runs down the center of the lower surface 428 of the card 402 and parallel with respect to the biosample connector 228a for a distance, then forms a larger semi-circular loop around the additive connector 282a (which forms an almost circular loop around the cylindrical stop 421) near the outer periphery 430 of the card 402, said loop at least partially formed and held in place via the semi-circular flushing connector canal 465 formed on the lower surface 428 of the card 402. The second end 272a of the flushing connector 254a connects to the fourth needle 440 via the directly adjacent needle connector 457.

Also on the lower surface 428 of the card 402, the additive connector 282a has a first end 284a and a second end 286a. The first end 284a connects to the third needle 438 via the directly adjacent needle connector 457. The second end 286a of the additive connector 282a connects to the second needle 436 via the directly adjacent needle connector 457. The additive connector 282a flushes an additive to the biosample container 220a as described in detail herein. The additive connector 282a forms an almost circular loop around the first aperture 460 (and the cylindrical stop 421 which extends through the card 402), said loop at least partially formed and held in place via the near semi-circular additive connector canal 466 formed on the lower surface 428 of the card 402.

The biosample connector 228a, the flushing connector 254a and the additive connector 282a are usually made from an elastomeric tubing which permits the biosample to be flushed to the container compartment 208a without retaining any significant number of cell samples within the tubing after flushing. Further, the elastomeric tubing is connected to the card 402 via a cyanoacrylate glue. Therefore, the tubing must connect to the card without disintegrating or otherwise becoming compromised by the attachment to the card 402. Tygon tubing No. R-1,000 made by Norton Company, P.O. Box 3660, Akron, Ohio, 44309-3660, is often utilized, although it will be appreciated that other suitable tubing is also commercially available. The card 402 is formed from any suitable plastic, acrylic, or other suitable material known in the art which will permit the card 402 to function as described herein. It will be further appreciated that each of the connectors may be formed as part of the card 402.

The lower surface 38a of the pump housing 14a further comprises a modified trigger 56a, a modified rod support member 160a, and a modified container compartment 208a, which fits within the pump housing component space 93a and connects to the second end 424 of the card 402. The modification of these components are described in detail below.

Referring to FIGS. 21 and 28–30, the trigger 56a is identical to the trigger 56 previously shown and described in detail herein, except that the upper end 62a is rounded. Further, in this embodiment, there is no trigger slide aperture 82 or trigger slide 74, or control member 124. In this embodiment, the upper end 62a of the trigger 56a is pivotally disposed such that the upper end 62a compresses the flushing connector 254a (interrupt position) when the finger surface 64a of the lower end 60a of the trigger 56a is not depressed. When the finger surface 64a of the lower end 60a of the trigger 56a is depressed, the upper end 62a of the trigger 56a pivots downward, away from the flushing connector 254a (enable position), thereby decompressing the flushing connector 254a and permitting the flushing solution to flow through the flushing connector 254a in order to move a biosample to the biosample container 220a in the container compartment 208a.

It will be appreciated that, as previously described herein, when the finger surface 64a of the lower end 60a of the trigger 56a is depressed toward the handle housing front surface 28a, contacting the microswitch button 58a to establish the on position for the trigger 56a, the flushing solution is permitted to flow through the flushing connector 254a because by pressing the trigger 56a, the operator is both causing the decompression of the flushing connector 254a thereby permitting a flushing solution to flow through the flushing connector 254a and simultaneously activating the pump, causing a vacuum and a suction to be created in the biosample connector 228a and the flushing connector 254a, thereby drawing the flushing solution from the flushing container 262a and through the flushing connector 254a to the biosample connector 228a and into the collection space 222a of the biosample container 220a. The microswitch button 58a, which activates the pump, is moved into the closed position, and into the open position, in the manner and by the method described previously herein.

Turning now to FIGS. 21, 25 and 28–34, a modified shaft 36a, identical to the shaft 36 shown and described previously in detail herein except that the shaft 36a extends through a rod support member base 467 and is engagingly received in the support post aperture 170a of the modified rod support member 160a, and is connected via a plurality of rod support member bolts 468 (only one of plurality of bolts illustrated in FIGS. 21 and 34 and designated 468) to the rod support member center 470. The modified rod support member 160a is seated on a rod support member base 467 which is disposed atop the lower surface 38a of the pump housing 14a. The rod support member base 467 provides a base for the rod support member 160a to rotate in a horizontal plane. The modified rod support member 160a is identical to the rod support member 160 previously shown and described herein, except that the rod support member 160a does not comprises a support post 172, the modified rod support member 160a comprises instead a round disk 472 having an upper surface 474, a lower surface 476, an outer peripheral flange 478, and an inner circular flange 480. The center of the rod support member 160a comprises an aperture 170a sized to engagingly receive the shaft 36a. The shaft 36a is engagingly connected to the rod support member 160a via any method or means shown and described herein or known in the art. The outer peripheral flange 478 of the rod support member 160a further comprises a plurality of flange slots 482 (only one such flange slot designated by the numeral 482). The inner circular flange 480 of the rod support member 160a further comprises a plurality of flange notches 484 (only one flange notch designated by the numeral 484). It will be appreciated that the plurality of flange slots 482 in the outer peripheral flange 478 correspond and generally align with the plurality of flange notches 484 in the inner circular flange 480. The rod support member 160a further comprises a first channel 486 and a second channel 488 both of which extend from the inner circular flange 480 across the upper surface 474 of the round disk 472 and through the outer peripheral flange 478. These first and second channels 486 and 488, respectively, as shown in FIGS. 31–32, permit adjustment of the connection of the shaft 36a to the rod support member 160a and the rod support center 470 via the plurality of rod support member bolts 468, and permit access, via removal of the rod support member 160a, to the shaft 36a.

The rod support member 160a has a plurality of rods 198a (FIGS. 31 and 33) which are identical to the plurality of rods 198 shown and described previously herein, except that the rods 198a are disposed via either the upper end 204a or the lower end 206a of the rod 198a in the one of the plurality of flange slots 482, while the opposite end of the rod 198a is disposed in the corresponding flange notch 484 in the inner circular flange 480, as shown in FIG. 31. The plurality of rods 198a are therefore disposed horizontally in the rod support member 160a, and rotate on this horizontal axis such that the outer periphery 202a of each of the plurality of rods 198a will rollingly engage and compress the flushing connector 254a, the biosample connector 228a, and the additive connector 282a when the pump is activated by an operator depressing the trigger 56a, as described herein. It will be appreciated that any number of rods 198a may be utilized, as long as the plurality of rods 198a function in the manner described herein.

The container compartment 208a as shown in FIGS. 21, 24 and 35–36 is a identical to the container compartment 208 previously shown and described herein, except that the container compartment 208a is a separate, self-container unit which is removable from the biosample aspirator 10a, the pump housing 14a and the card 402, and which fits within the pump component space 93a of the biosample aspirator 10a. The modified container compartment 208a has a first side 490, a second side 492, a front side 494, a back side 496, an upper side 498, and a lower side 500. The container compartment has a container space 501 in which resides the biosample container 220a, the flushing container 262a and the additive container 278a. Located in the front side 494 of the container compartment 208a is the first biosample adapter 502, the second additive adapter 504, the first additive adapter 506, and the first flushing adapter 508. All adapters described herein comprise adapters known and used in liquid medication bottles and/or intravenous solution bags/bottles, which permit a needle or similar device interface with the liquid/solution. Such adapters may comprise any other adapter known in the art for similar or identical interfaces, as illustrated in FIGS. 24 and 35. The first biosample adapter 502 is connected to the biosample container 220a. The second additive adapter 504 is connected to the biosample container 220a. The first additive adapter 506 is connected to the additive container 278a. The first flushing adapter 508 is connected to the flushing container 262a.

Turning now to FIG. 36, the second end 232a of the biosample connector 228a via the first needle 434 and adjacent needle connector 457 is connected to the biosample container 220a when the first needle 434 pierces the first biosample adapter 502. The second end 272a of the flushing connector 254a via the fourth needle 440 and adjacent needle connector 457 is connected to the flushing container 262a when the fourth needle 440 pierces the first flushing adapter 508. The first end 284a of the additive connector 282a via the third needle 438 and adjacent needle connector 457 is connected to the first additive container 278a when the third needle 438 pierces the first additive adapter 506. The second end 286a (not shown in FIG. 36) of the additive connector 282a via the second needle 436 and adjacent needle connector 457 is connected to the biosample container 220a via the second additive adapter 504.

Turning now to the modified additive button 322a, shown in FIGS. 21, 22 and 36 disposed via the plurality of slots 422 in the upper surface 404 of the hinged lid 400, the additive button 322a comprises a thumb wheel 510 having a rounded spoke 512, the rounded spoke 512 which extends through the oval slot 458 of the card 402 to compressingly engage the additive connector 282a near the second end 286a thereof, as illustrated in FIG. 21. When the thumb wheel 510 of the additive button 322a is rotated away from the operator by the operator's thumb, the spoke 512 rotates downward, perpendicular to the additive connector 282a, to compressingly engage the additive connector 282a such that no additive solution may flow to the second end 286a of the additive connector 282a when the spoke 512 is in compressing engagement therewith. When the thumbwheel 510 is rotated toward the operator by the operator's thumb, the spoke 512 rotates away from the additive connector 282a, thereby releasing the compression thereon, and permitting additive solution to flow to and through the second end 286a of the additive connector 282a. In this manner, the operator is permitted to choose whether to have an additive solution contained in the biosample container 220a with the biosample.

The reversing switch 403 is located on the back surface 30a of the housing handle 12a, as shown in FIG. 21. The reversing switch 403 causes the shaft 36a to rotate in a counter-clockwise manner, when the reversing switch 403 is depressed, causing the rod support member 160a and the rods 198a contained therein to rotate in a reverse (counter clockwise) fashion. A spring loaded door 518 covers the reversing switch 403 so that the reversing switch 403 will not be inadvertently activated during the operation of the biosample aspirator 10a. That is, one hand is required to hold open the spring-loaded door 518, while the other hand is required to hold the biosample aspirator 10a and activate the reverse switch 403. When the reverse switch 403 is depressed, the biosample contained in the biosample container 220a is aspirated via the biosample connector 228a out of the needle 16a opening. Therefore, at least a portion of the biosample is then immediately available for inspection by a pathologist or other appropriate personnel.

Referring now to FIGS. 21, 28–30 and 35–36, in operation the card 402 is disposed in the pump housing component space 93a such that the lower surface 428 of the card 402 is adjacent the modified lower surface 38a of the pump housing 14a, and the upper surface 426 of the card 402 is adjacent the lower surface 406 of the hinged lid 400. The modified container compartment 208a is then connected to the card 402 in the manner described previously herein (FIGS. 35–36). The hinged lid 400 is then connected to the lower surface 38a of the pump housing 14a via the connecting element 417 which has a reciprocal engaging element 418 for engagingly connecting the hinged lid 400 to the pump housing 14a (FIGS. 21). Said connection causes the upper end 62a of the trigger 56a to compressingly engage the biosample connector 228a and/or the flushing connector 254a. Further, said connection causes the modified additive button 322a via the thumb wheel 510 and particularly the rounded spoke 512 thereon to compressingly engage the additive connector 282a near the second end 286a thereof, when in the appropriate position, as previously described herein.

An operator grips the biosample aspirator 10a in one hand and positions the first end 18a of the needle 16a (not shown) in the desired biosite such as, but not by way of limitation, the prostate gland. The first end 18a of the needle 16a cuttingly engages the prostate gland and receives a tissue biosample in the opening of the first end 18 thereof. The trigger 56a is then pressed by the operator which activates the pump. The pump causes the rod support member 160a to rotate horizontally, generally in a clockwise fashion. The biosample connector 228a, the flushing connector 254a and the additive connector 282a all loop in a semicircular (the biosample connector 282a and the flushing connector 254a) or near circular (the additive connector 282a) manner on the lower surface 428 of the card 402, thereby permitting a compressing engagement of said connectors directly against the rod support member 160a and the plurality of rods 198a contained thereon. The biosample connector 228a, the flushing connector 254a, and the additive connector 282a are held in a continuing compressing engagement by the card 402 against the plurality of rods 198a. The outer periphery 202a of the rods 198a both rollingly and compressingly engage the biosample connector 228a, the flushing connector 254a, and the additive connector 282a, causing a vacuum and a suction to be formed within these three referenced connectors, said vacuum being formed in a clockwise direction such that, for example, the flushing solution flows from the flushing container 262a through the flushing connector 254a through the conduit 236a to the biosample connector 228a and into the biosample container 220a, and the additive solution, when utilized, flows from the additive container 278a through the additive connector 282a to the biosample container 220a.

When the trigger 56a is depressed, the upper end 62a of the trigger 56a is moved away from a compressing engagement with the biosample connector 228a and/or the flushing connector 254a (either connector or both connectors capable of being compressed) such that the vacuum created by the rolling and compressing action of the plurality of rods 198a and the clockwise rotation of the rod support member 160a against the afore-mentioned connectors causes a vacuum and suction therein, and also thereby causes the biosample to be both drawn from the needle 16a into the biosample connector 228a and flushed (via both the suction in the biosample connector 228a and the suction of the flushing solution which is drawn from the flushing container 262a through the flushing connector 254a) through the biosample connector 228a and into the biosample collection space 222a of the biosample container 220a. It will be appreciated that the vacuum which is established by the pump is capable of providing a continuous suction in the biosample connector 228a and in the needle opening.

When the modified additive button 322a (i.e., the thumbwheel 510 with spoke 512) is released, thereby releasing the compression of the spoke 512 from the additive connector 282a, a suction due to the vacuum created by the action of the pump, plurality of rods 198a, and the rotation of rod support member 160a against the additive connector 282a, as described herein, causes the additive solution to be drawn from the additive container 278a, the suction causing the additive solution to flow through the additive connector 282a to the biosample collection space 222a of the biosample container 220a. The additive may be any additive and/or fixative agent described herein and/or known in the art. It will be appreciated that many additive agents and many fixative agents are known in the art, and the term "additive", as used herein, encompasses either an additive, or, alternatively, a fixative, or, in a further alternative, both an additive and a fixative. The present invention is especially useful if the additive or additives can identify a condition in the biosample which aids in the immediate diagnosis of the patient. This would eliminate the time and expense of the biosample being analyzed in the laboratory or for the pathologist to be present in the operating room and/or area.

After the first biosample is delivered to the biosample collection space 222a, multiple biosamples may be obtained by repositioning the first end 18a of the needle 16a to obtain the next desired biosample. It will be appreciated that the needle 16a may be replaced after each use with another needle 16a or any appropriate needle known in the art. It will also be appreciated that a new card 402 may be inserted into the biosample aspirator 10a, to assist in the collection of additional or different biosamples. The card 402 is removed by simply reversing the steps for insertion of the card, as will be appreciated by those having ordinary skill in the art. Similarly, a new container compartment 208a may also be utilized for each additional sample. Alternatively, only a new card 402, or a new collection compartment 208a may be utilized. The previous card 402 may be discarded, or alternatively, may be properly cleaned with agents and/or processes well known in the art to prepare the card 402 for additional use. The container compartment 208a may similarly be discarded, usually after at least a portion of the biosample is withdrawn. Alternatively, the container compartment 208a (and all containers container therein, as described herein) may be cleaned with agents and/or processes well known in the art to prepare the container compartment 208a for additional use. It will be appreciated that the disposable aspect of the card 402 and the container compartment 208a enhances the feasibility of use of the biosample aspirator 10a, and makes the biosample aspirator 10a both more time efficient and more economically feasible, especially for repeated uses at close time intervals on a variety of patients, or on a variety of sites on a single patient, or both.

The biosample contained within the biosample aspirator 10a is removed by removing the container compartment 208a and providing said container compartment 208a to a laboratory in order to remove the biosample contained therein for analysis. After each biosample is obtained, the trigger 56a is then returned to the off position and the needle 16a of the biosample aspirator 10a is withdrawn from the biosite. It will be appreciated that when the container compartment 208a is detached from the card 402 and sent to the laboratory for appropriate analysis of the biosample, the biosample may be viewed through the clear plastic container compartment for the appropriate response, depending upon the additive used. Alternatively, the response may be ascertained by the operator or by one having ordinary skill in the art of ascertaining such responses (i.e., for example, a pathologist), soon after the biosample is collected and retained within the biosample collection space 222a of the biosample container 220a.

It will be appreciated that the biosample may be removed from the biosample collection space 222a of the biosample container 220a by aspirating the biosample out of the biosample container 220a via a needle and syringe, or by utilizing the reverse switch 403 as described herein to aspirate at least a portion of the biosample for evaluation, or by any other method, means and/or device known in the art. It will be appreciated, therefore, that laboratory personnel need never touch the biosample.

Changes may be made in the construction and operation of the various parts, elements and assemblies described herein and in the steps or in the sequence of steps of the methods described herein without departing from the spirit and scope of the invention as defined in the following claims.

What is claimed is:

1. An aspirator adapted for use in collecting a biosample and for use with a needle having a first end and a second end with a needle opening extending therethrough intersecting the first and the second ends thereof, comprising:

a biosample collection system comprising:
  a biosample collection section comprising a container compartment having a biosample container therein, the biosample container having a collection space sized to receive a biosample,
  wherein the biosample collection section is separable from the biosample collection system;
  a communication section for establishing fluidic communication between the needle opening and the biosample collection section comprising:
    a card having a biosample connector, the biosample connector having an outer periphery, a first end and a second end with a connector opening extending therethrough intersecting the first and the second ends thereof, the first end of the biosample connector being connectable to the second end of the needle and the second end of the biosample connector being connected to the biosample container with the connector opening being in fluidic communication with the needle opening and with the collection space in the biosample container, and
    wherein the communication section is separable from the biosample collection system;
  suction means for generating and establishing a vacuum and being capable of continuous suction in the biosample collection system whereby a biosample received via the first end of the needle is movably transferred through the needle opening and the communication system and into the biosample collection section, comprising:
    a pump connected to the biosample collection system for generating and establishing a vacuum generally within the needle opening and the connector opening whereby the biosample is sucked through the needle opening and through the connector opening and into the collection space in the biosample container in a driven condition of the pump;
    drive means connected to the pump for activating the pump in the driven condition;
    a pump housing having a first end, a second end and a pump housing component space formed generally between the first end and the second end of the pump housing, the pump housing having an upper surface comprising a hinged lid and a lower surface, the communication section being disposed in the pump housing component space and extending generally between the first end and the second end of the pump housing, the second end of the needle being connectable to the first end of the biosample connector in the communication section and the needle being extendable a distance generally from the first end of the pump housing, the biosample collection section being disposed in the pump housing component space near the second end of the pump housing, the biosample container therein being connected to the second end of the biosample connector generally near the second end of the pump housing, the pump being disposed in the pump housing component space; and a handle housing adapted to be gripped by an individual when the aspirator is being used for obtaining a biosample, having an upper end and a lower end, a handle component space being formed in a portion of the handle, a portion of the drive means being disposed generally within the handle component space and a portion of the drive means extending from the handle component space a distance generally above the upper end of the handle housing and being connected with the pump in the pump housing component space.

2. The aspirator of claim 1 wherein the biosample connector comprises an elastomeric tubing.

3. The aspirator of claim 1 wherein the drive means comprises:

a motor connected to the pump for activating the pump in a driven condition in an on condition of the motor and means for selectively activating the motor in the on condition.

4. The aspirator of claim 1 wherein the pump comprises:

a plurality of cylindrically shaped rods, each rod having opposite ends and an outer peripheral surface; and means for supporting the rods in a generally circular configuration with each rod being spaced a distance from adjacent rods, the pump being positioned so the outer peripheral surface of at least one of the rods is engageable with the outer peripheral surface of the biosample connector and so the outer peripheral surfaces of each of the rods alternately engages the outer peripheral surface of the biosample connector in the driven condition of the pump, the rods being rotated in the driven condition of the pump and the outer peripheral surface of the rods alternately engaging the biosample connector for generating and establishing the vacuum in the connector opening and the needle opening in the driven condition of the pump.

5. The aspirator of claim 1 wherein the pump is defined further as being a peristaltic pump.

6. The aspirator of claim 4 wherein the means for supporting the rods is disposed in a horizontal plane.

7. The aspirator of claim 1 wherein the pump is connectable to the biosample container in communication with the collection space for creating a vacuum generally within the collection space, the connector opening and the needle opening in a driven condition of the pump.

8. The aspirator of claim 1 wherein the drive means comprises:

a motor connectable to the pump for activating the pump in a driven condition in an on condition of the motor;

means for selectively activating the motor in the on condition;

battery means disposed in the handle component space in electrical continuity with the motor; and a switch having an opened and a closed position interposed between the battery means and the motor for establishing electrical continuity between the battery means and the motor whereby the motor is activated in the on condition in the closed position of the switch, and for interrupting electrical continuity between the battery means and the motor whereby the motor is in an off condition in the opened position of the switch.

9. The aspirator of claim 8 wherein the means for selectively activating the motor comprises:

a trigger movably connected to one of the pump housing and the handle housing, the trigger being engageable with the switch, and the trigger being engageable by an individual for movement to an on position and the trigger causing the switch to be moved to the closed position in the on position of the trigger.

10. The aspirator of claim 1 further comprising:

a flushing container having a flushing substance space formed in a portion thereof for retaining a quantity of flushing substance; and means for establishing fluidic communication between the flushing substance space and at least one of the needle opening and the biosample connector opening for moving flushing substances from the flushing substance space and into the connector opening for aiding the delivery of the biosample through the connector opening and into the collection space in the biosample container; and means for interrupting communication between the flushing substance space and the biosample connector opening whereby the flushing substance is prevented from passing from the flushing substance space and into the collector opening in the biosample connector.

11. The aspirator of claim 10 wherein the means for establishing fluidic communication comprises:

a pump adapted to generate and establish a vacuum generally within the needle opening and the biosample connector opening and for establishing a vacuum for sucking flushing substance from the flushing substance container when communication is established between the flushing substance space and at least one of the needle opening and the connector opening, whereby the biosample is sucked through the needle opening and through the biosample connector opening and into the collection space in the biosample container in a driven condition of the pump and whereby flushing substance is sucked from the flushing substance space and into the connector opening in the biosample connector when communication is established between the flushing substance space and at least one of the biosample connector opening in the biosample connector and the needle opening; and drive means connected to the pump for activating the pump in a driven condition.

12. The aspirator of claim 11 wherein the drive means comprises:

a motor connectable to the pump for activating the pump in a driven condition in an on condition of the motor; and means for selectively activating the motor in the on condition.

13. The aspirator of claim 11 wherein the pump is defined further as being adapted to generate and establish a vacuum generally within the needle opening and the connector opening and for establishing a vacuum for sucking flushing substance from the flushing substance container when communication is established between the flushing substance space and at least one of the needle opening and the connector opening, whereby the biosample is sucked through the needle opening and through the connector opening and into the collection space in the biosample container in a driven condition of the pump and whereby flushing substance is sucked from the flushing substance space and into the connector opening in the biosample connector when communication is established between the flushing substance space and at least one of the connector opening in the biosample connector and the needle opening; and drive means connected to the pump for activating the pump in a driven condition.

14. The aspirator of claim 10 wherein the means for establishing fluidic communication between the flushing substance space and at least one of the needle opening and the biosample connector opening further comprises:

a card having a flushing connector, the flushing connector having an outer periphery, a first end and a second end, a connector opening being formed through the flushing connector intersecting the first and the second ends thereof, the second end of the flushing connector being connected to the flushing container with the connector opening in the flushing connector being in communication with the flushing substance space in the flushing container and the first end of the flushing connector being connectable to one of the biosample connector and the needle opening so the connector opening in the flushing connector is in communication with the connector opening in the biosample connector.

15. The aspirator of claim 14 wherein the pump comprises:

a plurality of cylindrical shaped rods, each rod having opposite ends and an outer peripheral surface; and means for supporting the rods in a generally circular configuration with each rod being spaced a distance from adjacent rods, the pump being positioned so the outer peripheral surface of at least one of the rods is engageable with the biosample connector and so the outer peripheral surfaces of each of the rods alternately engages the biosample connector in a driven condition of the pump, the rods being rotated in a driven condition of the pump and the outer peripheral surface of the rods alternately engaging the biosample connector thereby creating a vacuum in the connector opening in the biosample connector, the flushing connector and the needle opening in a driven condition of the pump, whereby the flushing substance is passed from the flushing substance space through the connector opening in the flushing connector and into the connector opening in the biosample connector when communication is established between the flushing substance space and the connector opening of the biosample connector by way of the connector opening in the flushing connector.

16. The aspirator of claim 15 wherein the pump is defined further as being a peristaltic pump.

17. The aspirator of claim 1 further comprising:

an additive container having an additive space formed in a portion thereof for retaining a quantity of an additive; and means for establishing communication between the additive means in the additive container and the collection space in the biosample container and for interrupting communication between the additive space in the additive container and the collection space in the biosample container, the additive being passable from the additive space into the collection space when communication is established between the additive space in the additive container and the collection space in the biosample container.

18. The aspirator of claim 17 wherein the means for establishing communication between the additive space in the additive container and the collection space in the biosample container further comprises:

a card having an additive connector, the additive connector having an outer periphery, a first end, a second end and a connector opening extending therethrough intersecting the first and the second ends thereof, the first end of the additive connector being connected to the additive container with the connector opening being in fluidic communication with the additive space in the additive container and the second end being connected to the biosample container with the additive opening being in fluidic communication with the collection space in the biosample container.

19. The aspirator of claim 18 wherein the means for establishing communication further comprises:

a pump adapted to generate and establish a vacuum generally within the needle opening and the biosample connector opening and for establishing a vacuum for sucking additive from the additive space when communication is established between the additive space and the collection space, whereby the biosample is sucked through the needle opening and through the connector opening and into the collection space in the biosample container in a driven condition of the pump and whereby additive is sucked from the additive space and passed into the collection space in a driven condition of the pump and when communication is established between the additive space and the collection space;

drive means connected to the pump for activating the pump in a driven condition.

20. The aspirator of claim 19 wherein the drive means comprises:

a motor connectable to the pump for activating the pump in a driven condition in an on condition of the motor; and means for selectively activating the motor in the on condition.

21. The aspirator of claim 19 wherein the pump comprises:

a plurality of cylindrically shaped rods, each rod having opposite ends and an outer peripheral surface; and means for supporting the rods in a generally circular configuration with each rod being spaced a distance from adjacent rods, the pump being positioned so the outer peripheral surface of at least one of the rods is engageable with the biosample connector and so the outer peripheral surfaces of each of the rods alternately engages the biosample connector in a driven condition of the pump, the rods being rotated in a driven condition of the pump and the outer peripheral surface of the rods alternately engaging the biosample connector thereby creating a vacuum in the connector opening in the biosample connector and the needle opening in a driven condition of the pump and the pump being positioned so that the outer peripheral surface of at least one of the rods is engageable with the outer peripheral surface of the additive connector and the outer peripheral surface of the rods alternately engaging the additive connector opening whereby additive is passed from the additive space through the connector opening and into the collection space in the biosample container when communication is established between the additive space and the collection space.

22. The aspirator of claim 21 wherein the pump is defined further as being a peristaltic pump.

23. The aspirator of claim 17 wherein the means for establishing communication between the additive space and the collection space is defined further as means capable of regulatably establishing communication between the additive space and the collection space for controlling the amount of additive being passed from the additive space into the collection space.

24. The aspirator of claim 2 wherein the means for regulatably establishing communication between the additive space and the collection space is defined further as comprising:

a regulator engageable with the outer peripheral surface of the additive connector for selectively compressing the connector opening, the degree to which the connector opening is compressed controlling the amount of additive being passed through the additive connector from the additive space into the collection space; and means for moving the regulator into engagement with the outer peripheral surface of the additive connector for selectively compressing the connector opening in the additive connector.

25. The aspirator of claim 17 further comprising:

a flushing container having a flushing substance space formed in a portion thereof for retaining a quantity of flushing substance; and means for establishing fluidic communication between the flushing substance space and at least one of the needle opening and the biosample connector opening for moving flushing substances from the flushing substance space and into the biosample connector opening for aiding the delivery of the biosample through the biosample connector opening and into the collection space in the biosample container, and for interrupting communication between the flushing substance space and the biosample connector opening whereby the flushing substance is prevented from passing from the flushing substance space and into the connector opening in the biosample connector.

26. The aspirator of claim 25 wherein the means for establishing communication further comprises:

a pump adapted to generate and establish a vacuum generally within the needle opening and the biosample connector opening and for establishing a vacuum for sucking flushing substance from the flushing substance container when communication is established between the flushing substance space and at least one of the needle opening and the connector opening whereby the biosample is sucked through the needle opening and through the connector opening and into the collection space in the biosample container in a driven condition of the pump, and whereby flushing substance is sucked from the flushing substance space and into the connector opening in the biosample connector when communication is established between the flushing substance space and at least one of the connector opening in the biosample connector and the needle opening, the pump also being adapted to establish a vacuum in the connector opening in the additive connector whereby additive is sucked from the additive space and passed through the connector and into the collection space in the biosample container; and drive means connected to the pump for activating the pump in a driven condition.

27. The aspirator of claim 26 wherein the drive means comprises:

a motor connectable to the pump for activating the pump in a driven condition in an on condition of the motor; and means for selectively activating the motor in the on condition.

28. The aspirator of claim 25 wherein the means for establishing communication between the flushing substance space and at least one of the needle opening and the biosample connector opening further comprises:

a card having a flushing connector, the flushing connector having an outer periphery, a first end and a second end, a connector opening being formed through the flushing connector intersecting the first and the second ends thereof, the second end of the flushing connector being connected to the flushing container with the connector opening in the flushing connector being in communication with the flushing substance space in the flushing container and the first end of the flushing connector being connectable to one of the biosample connector and the needle opening so that connector opening in the flushing connector is in communication with the connector opening in the biosample connector.

29. The aspirator of claim 26 wherein the pump comprises:

a plurality of cylindrically shaped rods, each rod having opposite ends and an outer peripheral surface; and means for supporting the rods in a generally circular configuration with each rod being spaced a distance from adjacent rods, the pump being positioned so the outer peripheral surface of at least one of the rods is engageable with the biosample connector and so the outer peripheral surfaces of each of the rods alternately engages the biosample connector in a driven condition of the pump, the rods being rotated in a driven condition of the pump and the outer peripheral surface of the rods alternately engaging the biosample connector thereby creating a vacuum in the connector opening in the biosample connector, the connector opening in the flushing connector and the needle opening in a driven condition of the pump, whereby the flushing substance is passed from the flushing substance space through the connector opening in the flushing connector and into the connector opening in the biosample connector when communication is established between the flushing substance space and the connector opening of the biosample connector by way of the connector opening in the flushing connector, the pump being positioned so the outer peripheral surface of at least one of the rods is engageable with the outer peripheral surface of the additive connector and the outer peripheral surface of the rods alternately engaging the additive connector for establishing a vacuum in the connector opening whereby additive is passed from the additive space through the additive connector opening and into the collection 38 space when communication is established between the additive space and the collection space.

30. The aspirator of claim 29 wherein the pump is defined further as being a peristaltic pump.

31. The aspirator of claim 28 wherein the means for establishing communication between the flushing substance space and the connector opening in the biosample connector and for interrupting communication between the flushing substance space and the connector opening in the biosample connector further comprises:

a control member movably disposed in the pump housing component space, the control member being movable from an enable position to an interrupt position, the control member engaging the outer peripheral surface of the flushing connector and compressing the flushing connector to close the flushing connector opening in the interrupt position of the control member and the control member being disengaged from the flushing connector sufficiently so that the connector opening in the flushing connector is opened thereby establishing communication between the flushing space and the connector opening in the biosample connector by way of the connector opening in the flushing connector in the enable position of the control member; and means for moving the control member from the enable position to the interrupt position and from moving the control member from the interrupt position to the enable position.

32. The aspirator of claim 26 wherein the drive means comprises:

a motor connectable to the pump for activating the pump in a driven condition in an on condition of the motor;

means for selectively activating the motor in the on condition;

battery means disposed in the handle component space in electrical continuity with the motor; and a switch having an opened and a closed position interposed between the battery means and the motor for establishing electrical continuity between the battery means and the motor whereby the motor is activated in the on condition in the closed position of the switch, and for interrupting electrical continuity between the battery means and the motor whereby the motor is in an off condition in the opened position of the switch.

33. The aspirator of claim 32 wherein the drive means further comprises:

a trigger movably connected to one of the pump housing and the handle housing, the trigger being engageable with the switch, and the trigger being engageable by an individual for movement to an on position and the trigger causing the switch to be moved to the closed position in the on position of the trigger.

34. The aspirator of claim 33 wherein the trigger is defined further as being connected to the control member for selectively moving the control member to the enable position after the trigger has been moved to the on position.

35. The aspirator of claim 1 wherein the card is both disposable in the pump housing component space and removable from the pump housing component space.

36. The aspirator of claim 1 wherein the container compartment is connectable to the card and the biosample connector, the flushing connector and the additive connector via connecting means.

37. The aspirator of claim 1 wherein the hinged lid hingably connects to pivot upward, permitting the card to be disposed therein, and wherein the hinged lid has connecting means for firmly connecting the hinged lid to the pump housing.

38. An aspirator adapted for use in collecting a biosample and for use with a needle having a first end and a second end with a needle opening extending therethrough intersecting the first and the second ends thereof, comprising:

a biosample collection system comprising:

a biosample collection section comprising a container compartment having a biosample container therein, the biosample container having a collection space sized to receive a biosample, wherein the biosample collection section is separable from the biosample collection system;

a communication section for establishing fluidic communication between the needle opening and the biosample collection section comprising:

a card having both a biosample connector and a flushing connector, the biosample connector having an outer periphery, a first end and a second end with a connector opening extending therethrough intersecting the first and the second ends thereof, the first end of the biosample connector being connectable to the second end of the needle and the second end of the biosample connector being connected to the biosample container with the connector opening being in fluidic communication with the needle opening and with the collection space in the biosample container;

wherein the communication section is separable from the biosample collection system;

suction means for generating and establishing a vacuum and being capable of continuous suction in the biosample collection system whereby a biosample received via the first end of the needle is movably transferred through the needle opening and the communication system and into the biosample collection section;

a flushing container having a flushing substance space formed in a portion thereof for retaining a quantity of flushing substance; and means for establishing fluidic communication between the flushing substance space and at least one of the needle opening and the biosample connector opening for moving flushing substances from the flushing substance space and into the connector opening for aiding the delivery of the biosample through the connector opening and into the collection space in the biosample container, and for interrupting communication between the flushing substance space and the biosample connector opening whereby the flushing substance is prevented from passing from the flushing substance space and into the collector opening in the biosample connector, comprising:

the flushing connector having an outer periphery, a first end and a second end, a connector opening being formed through the flushing connector intersecting the first and the second ends thereof, the second end of the flushing connector being connected to the flushing container with the connector opening in the flushing connector being in communication with the flushing substance space in the flushing container and the first end of the flushing connector being connectable to one of the biosample connector and the needle opening so that connector opening in the flushing connector is in communication with the connector opening in the biosample connector;

said suction means comprising a pump adapted to generate and establish a vacuum generally within the needle opening and the biosample connector opening and for establishing a vacuum for sucking flushing substance from the flushing substance container when communication is established between the flushing substance space and at least one of needle opening and the connector opening, whereby the biosample is sucked through the needle opening and through the biosample connector opening and into the collection space in the biosample container in a driven condition of the pump and whereby flushing substance is sucked from the flushing substance space and into the connector opening in the biosample connector when communication is established between the flushing substance space and at least one of the connector opening in the biosample connector and the needle opening; and drive means connected to the pump for activating the pump in a driven condition, comprising:
a motor connectable to the pump for activating the pump in a driven condition in an on condition of the motor; and
means for selectively activating the motor in the on condition;

a pump housing having a first end, a second end and a pump housing component space formed generally between the first end and the second end of the pump housing, the pump housing having an upper surface comprising a hinged lid and a lower surface, the communication section being disposed in the pump housing component space and extending generally between the first end and the second end of the pump housing, the second end of the needle being connectable to the first end of the biosample connector in the communication section and the needle being extendable a distance generally from the first end of the pump housing, the biosample collection section being disposed in the pump housing component space near the second end of the pump housing, the biosample container therein being connected to the second end of the biosample connector generally near the second end of the pump housing, the pump being disposed in the pump housing component space, the flushing connector being connected to the second end of the flushing connector generally near the second end of the pump housing; and a handle housing adapted to be gripped by an individual when the aspirator is being used for obtaining a biosample, having an upper end and a lower end, a handle housing component space being formed in a portion of the handle, a portion of the drive means being disposed generally within the handle component space and a portion of the drive means extending from the handle component space a distance generally above the upper end of the handle housing and being connected with the pump in the pump housing component space.

39. The aspirator of claim 38 wherein the means for establishing communication between the flushing substance space and the connector opening in the biosample connector and for interrupting communication between the flushing substance space and the connector opening in the biosample connector further comprises:

a control member movably disposed in the pump housing component space, the control member being movable from an enable position to an interrupt position, the control member engaging the outer peripheral surface of the flushing connector and compressing the flushing connector to close the connector opening in the flushing connector in the interrupt position of the control member and the control member being disengaged from the flushing connector sufficiently so that the connector opening in the flushing connector is opened thereby establishing flushing cation between the flushing space and the connector opening in the biosample connector by way of the connector opening in the flushing connector in the enable position of the control member; and means for moving the control member from the enable position to the interrupt position and from moving the control member from the interrupt position to the enable position.

40. The aspirator of claim 38 wherein the drive means further comprises:

a motor connectable to the pump for conditioning the pump in a driven condition in an on condition of the motor;

means for selectively activating the motor in the on condition;

battery means disposed in the handle component space in electrical continuity with the motor; and a switch having an opened and a closed position interposed between the battery means and the motor for establishing electrical continuity between the battery means and the motor whereby the motor is activated in the on condition in the closed position of the switch, and for interrupting electrical continuity between the battery means and the motor whereby the motor is in an off condition in the opened position of the switch.

41. The aspirator of claim 40 wherein the drive means further comprises:

a trigger movably connected to one of the pump housing and the handle housing, the trigger being engageable with the switch, and the trigger being engageable by an individual for movement to an on position and the trigger causing the switch to be moved to the closed position in the on position of the trigger.

42. The aspirator of claim 41 wherein the trigger is defined further as being connected to the control member for selectively moving the control member to the enable position after the trigger has been moved to the on position.

43. The aspirator of claim 38 wherein the card is both disposable in the pump housing component space and removable from the pump housing component space.

44. The aspirator of claim 38 wherein the container compartment is connectable to the card and the biosample connector, the flushing connector and the additive connector via connecting means.

45. The aspirator of claim 38 wherein the hinged lid hingably connects to pivot upward, permitting the card to be disposed therein, and wherein the hinged lid has connecting means for firmly connecting the hinged lid to the pump housing.

46. An aspirator adapted for use in collecting a biosample and for use with a needle having a first end and a second end with a needle opening extending therethrough intersecting the first and the second ends thereof, comprising:

a biosample collection system comprising:
a biosample collection section comprising a container compartment having a biosample container therein, the biosample container having a collection space sized to receive a biosample,
wherein the biosample collection section is separable from the biosample collection system;
a communication section for establishing fluidic communication between the needle opening and the biosample collection section comprising:

a card having a biosample connector, a flushing connector, and an additive connector, the biosample connector having an outer periphery, a first end and a second end with a connector opening extending therethrough intersecting the first and the second ends thereof, the first end of the biosample connector being connectable to the second end of the needle and the second end of the biosample connector being connected to the biosample container with the connector opening being in fluidic communication with the needle opening and with the collection space in the biosample container; and wherein the communication section is separable from the biosample collection system;

suction means for generating and establishing a vacuum and being capable of continuous suction in the biosample collection system whereby a biosample received via the first end of the needle is movably transferred through the needle opening and the communication system and into the biosample collection section, comprising:

a pump connected to the biosample collection system for generating and establishing a vacuum generally within the needle opening and the connector opening whereby the biosample is sucked through the needle opening and through the connector opening and into the collection space in the biosample container in a driven condition of the pump; and drive means connected to the pump for activating the pump in the driven condition; an additive container having an additive space formed in a portion thereof for retaining a quantity of an additive; and means for establishing fluidic communication between the additive space in the additive container and the collection space in the biosample container and for interrupting communication between the additive space in the additive container and the collection space in the biosample container, the additive being passable from the additive space into the collection space when communication is established between the additive space in the additive container and the collection space in the biosample container, comprising:

the additive connector having an outer periphery, a first end, a second end and a connector opening extending therethrough intersecting the first and the second ends thereof, the first end of the additive connector being connected to the additive container with the connector opening being in fluidic communication with the additive space in the additive container and the second end being connected to the biosample container with the additive opening being in fluidic communication with the collection space in the biosample container;

a pump housing having a first end, a second end and a pump housing component space formed generally between the first end and the second end of the pump housing, the pump housing having an upper surface comprising a hinged lid and a lower surface, the communication section being disposed in the pump housing component space and extending generally between the first end and the second end of the pump housing, the second end of the needle being connectable to the first end of the biosample connector in the communication section and the needle being extendable a distance generally from the first end of the pump housing, the biosample collection section being disposed in the pump housing component space near the second end of the pump housing, the biosample container therein being connected to the second end of the biosample connector generally near the second end of the pump housing, the pump being disposed in the pump housing component space and extending generally between the additive container and the biosample container near the second end of the pump housing; and a handle housing adapted to be gripped by an individual when the aspirator is being used for obtaining a biosample, having an upper end and a lower end, a handle component space being formed in a portion of the handle housing, a portion of the drive means being disposed generally within the handle component space and a portion of the drive means extending from the handle component space a distance generally above the upper end of the handle housing and being connected with the pump in the pump housing component space.

47. The aspirator of claim 46 wherein the card is both disposable in the pump housing component space and removable from the pump housing component space.

48. The aspirator of claim 46 wherein the container compartment is connectable to the card and the biosample connector, the flushing connector and the additive connector via connecting means.

49. The aspirator of claim 46 wherein the hinged lid hingably connects to pivot upward, permitting the card to be disposed therein, and wherein the hinged lid has connecting means for firmly connecting the hinged lid to the pump housing.

50. A method for collecting a biosample at a selected biosite from a subject using an aspirator adapted for use in collecting a biosample and for use with a needle having a first end and a second end with a needle opening extending therethrough and intersecting the first and the second ends thereof, the biosample being collected in a biosample collection system in communication with the needle comprising:

providing a biosample collection system;

holding the biosample collection system in one hand, the biosample collection system being held in close proximity to the subject;

inserting the needle into the subject and positioning the first end of the needle at the selected biosite to receive the biosample;

receiving at least a portion of a biosample into the opening of the first end of the needle;

activating the biosample collection system to engage the biosample in the needle to permit transport of the biosample into the biosample collection system, wherein said step of providing comprises providing a biosample collection system comprising:

a biosample collection section comprising a container compartment having a biosample container having a biosample collection space adapted for receiving the biosample therein, a pump connected to the biosample collection space for establishing a suction means within the biosample collection system, a drive means connected to the pump for activating the pump in a driven condition, a communicating section comprising a card for establishing fluidic communication between the needle opening and the biosample collection area, an activating trigger connected to the drive means and the to the communicating section for activating the pump and fluidic communication between the needle opening and the biosample container, the card comprising a biosample connector having a first end and a second end and a connector opening extending therethrough intersecting the first and second ends thereof, the first end of the biosample connector engaging the second of the needle and the second end of the biosample connector engaging the biosample container, the biosample connector capable of transporting the biosample engaged in the needle to the biosample container; a pump housing having a first end, a second end and a pump housing component space formed generally between the first end and the second end of the pump housing, the pump housing having an upper surface comprising a hinged lid and a lower surface, the communication section being disposed in the pump housing component space and extending generally between the first end and the second end of the pump housing, the second end of the needle being connectable to the first end of the biosample connector and the needle being extendable a distance generally from the first end of the pump housing, the biosample collection section being disposed in the pump housing component space near the second end of the pump housing, the biosample container therein being connected to the second end of the biosample connector generally near the second end of the pump housing, the pump being disposed in the pump housing component space, and a handle housing adapted to be gripped by an individual when the aspirator is being used for obtaining a biosample having an upper end and a lower end, a handle component space being formed in a portion of the handle, a portion of the drive means being disposed generally within the handle component space and a portion of the drive means extending from the handle component space a distance generally above the upper end of the handle housing and being connected with the pump in the pump housing component space;

gripping the trigger, thereby activating the drive means of the pump and the communicating section, causing the pump to generate a suction, and causing fluidic communication between the needle and the biosample collection section to be generated;

establishing a vacuum capable of continuous suction in the biosample collection system;

aspirating a biosample from the first end of the needle and the needle opening and movably transferring the biosample through the needle opening and through the biosample connector to the biosample collection space, wherein the communicating section establishes fluidic communication between the needle and the biosample collection space to aid in the delivery of the biosample collection space.

51. The method of claim 50 further comprising cuttingly engaging the biosite to receive a biosample in the opening of the first end of the needle.

52. The method of claim 50 further comprising:

repositioning the first end of the needle, after inserting the needle in the subject and after collecting the first biosample, to position the first end of the needle at a second biosite to receive a biosample in the opening of the first end of the needle; and establishing a vacuum by way of the means capable of generating a continuous vacuum for sucking the second biosample collected at the second biosite through the needle opening and the biosample collection system.

53. The method of claim 52 further comprising:

repositioning the first end of the needle in the subject to be disposed near subsequent biosites, after collecting the second biosample; and establishing a vacuum at least at each time the first end of the needle is positioned at each subsequent biosite for sucking subsequent biosamples through the needle opening and into the biosample collection system.

54. The method of claim 52 wherein the biosample collection system comprises a biosample container having a collection space sized to receive at least one biosample.

55. The method of claim 54 further comprising:

adding at least one additive to the collection space.

56. The method of claim 50 further comprising:

flushing the biosample into the biosample collection system by introducing a flushing substance in a portion of the biosample collection system.

57. The method of claim 50 further comprising:

flushing the biosample into the biosample collection system by introducing a flushing substance in a portion of the needle opening.

58. The method of claim 50 wherein the biosample collection system further comprises:

removing the biosample collection section from the pump housing by disconnecting the biosample collection section from the card, and sending the biosample contained within the biosample collection section to a laboratory for analysis of the biosample.

59. The method of claim 50 wherein the biosample collection system further comprises:

opening the hinged lid of the pump housing removing the card.

60. The method of claim 50 wherein the biosample collection system further comprises:

activating the reverse switch by opening the door and pushing the switch; and aspirating the biosample containd within the collection space of the biosample container out of the needle opening.

* * * * *

UNITED STATES PATENT AND TRADEMARK OFFICE
CERTIFICATE OF CORRECTION

PATENT NO. : 5,669,394            Page 1 of 2

DATED : September 23, 1997

INVENTOR(S) : Bergey et al.

It is certified that error appears in the above-identified patent and that said Letters Patent is hereby corrected as shown below:

Cover page under [57] ABSTRACT, line 3, please delete "drive", and substitute therefor --driven--.

Column 1, lines 6-7, please delete "BIOSAMPLE ASPIRATOR", and substitute therefor --FLUSHING NEEDLE--.

Column 5, line 7, please delete "122", and substitute therefor --108--.

Column 8, line 16, please delete "238", and substitute therefor --242--.

Column 8, line 21, please delete "224", and substitute therefor --220--.

Column 10, line 14, after 'first end', please delete "336", and substitute therefor --337--.

Column 10, line 46, after 'shaft', please delete "340", and substitute therefor --343--.

UNITED STATES PATENT AND TRADEMARK OFFICE
CERTIFICATE OF CORRECTION

PATENT NO. : 5,669,394

DATED : September 23, 1997

INVENTOR(S) : Bergey et al.

It is certified that error appears in the above-identified patent and that said Letters Patent is hereby corrected as shown below:

Column 13, line 54, after 'lower surface', please delete "36a", and substitute therefor --38a--.

Column 16, line 2, please delete "comprises", and substitute therefor --comprise--.

Column 19, lines 3-4, please delete "thum-bwheel", and substitute therefor --thumb-wheel--.

Column 30, line 3, please delete "flushing cation", and substitute therefor --communication--.

Column 34, line 55, please delete "containd", and substitute therefor --contained--.

Signed and Sealed this

Tenth Day of March, 1998

Attest:

BRUCE LEHMAN

Attesting Officer

Commissioner of Patents and Trademarks